US011845974B2

(12) United States Patent
Koskinen et al.

(10) Patent No.: US 11,845,974 B2
(45) Date of Patent: Dec. 19, 2023

(54) METHODS FOR CONTINUOUS PRODUCTION OF PRODUCTS FROM MICROORGANISMS

(71) Applicant: NESTE CORPORATION, Espoo (FI)

(72) Inventors: Perttu Koskinen, Helsinki (FI); Heidi Vainio, Espoo (FI); Miia Laamanen, Porvoo (FI); Raisa Vermasvuori, Hinthaara (FI); Reijo Tanner, Hikiä (FI)

(73) Assignee: NESTE CORPORATION, Espoo (FI)

( * ) Notice: Subject to any disclaimer, the term of this patent is extended or adjusted under 35 U.S.C. 154(b) by 246 days.

(21) Appl. No.: 15/577,203

(22) PCT Filed: May 25, 2016

(86) PCT No.: PCT/FI2016/050360
§ 371 (c)(1),
(2) Date: Nov. 27, 2017

(87) PCT Pub. No.: WO2016/189203
PCT Pub. Date: Dec. 1, 2016

(65) Prior Publication Data
US 2018/0171371 A1  Jun. 21, 2018

(30) Foreign Application Priority Data

May 25, 2015  (FI) ...................... 20155385

(51) Int. Cl.
C12Q 3/00    (2006.01)
C12P 7/64    (2022.01)
C12M 1/00    (2006.01)
C12M 1/12    (2006.01)
C12M 1/06    (2006.01)

(52) U.S. Cl.
CPC ............... *C12P 7/64* (2013.01); *C12M 23/58* (2013.01); *C12M 25/18* (2013.01); *C12M 27/02* (2013.01)

(58) Field of Classification Search
CPC ........... C12P 7/64; C12M 25/18; C12M 23/58
See application file for complete search history.

(56) References Cited

U.S. PATENT DOCUMENTS

| | | |
|---|---|---|
| 5,874,263 A | 2/1999 | Holtzapple et al. |
| 5,962,307 A | 10/1999 | Holtzapple et al. |
| 6,596,521 B1 | 7/2003 | Chang et al. |
| 9,434,962 B2 | 9/2016 | Koskinen et al. |
| 2010/0041124 A1 | 2/2010 | Chang et al. |
| 2012/0156669 A1* | 6/2012 | Gonzalez ........... C12N 1/12 435/3 |
| 2012/0159839 A1 | 6/2012 | Koskinen et al. |
| 2012/0219993 A1 | 8/2012 | Chang et al. |
| 2013/0295623 A1* | 11/2013 | Gardner ............ C12N 1/12 435/134 |
| 2016/0186218 A1* | 6/2016 | Hafez ............... C12M 41/12 435/150 |

FOREIGN PATENT DOCUMENTS

| | | |
|---|---|---|
| CN | 102311912 A | 1/2012 |
| CN | 102994380 A | 3/2013 |
| GB | 2 125 064 A | 2/1984 |
| JP | 2013-183687 A | 9/2013 |
| WO | WO 1998/004729 A2 | 2/1998 |
| WO | WO 2012/085340 A1 | 6/2012 |

OTHER PUBLICATIONS

Shishido et al., JP 2013-183687; Publication Date: Sep. 19, 2013; English Machine Translation.*
Shishido et al., JP 2013-183687; Publication Date: Sep. 19, 2013; English Machine Translation (of record). (Year: 2013).*
Office Action dated Nov. 20, 2018, by the Japanese Patent Office in corresponding Japanese Patent Application No. 2018-513918, and an English Translation of the Office Action. (7 pages).
International Search Report (PCT/ISA/210) dated Jul. 25, 2016, by the European Patent Office as the International Searching Authority for International Application No. PCT/FI2016/050360.
Written Opinion (PCT/ISA/237) dated Jul. 25, 2016, by the European Patent Office as the International Searching Authority for International Application No. PCT/FI2016/050360.
Sitepu et al., Manipulation of culture conditions alters lipid content and fatty acid profiles of a wide variety of known and new oleaginous yeast species, *Bioresource Technology*, Jun. 28, 2013, pp. 360-369, vol. 144, Elsevier B.V. http://dx.doi.org/10.1016/j.biortech.2013.06.047.
Dias et al., New dual-stage pH control fed-batch cultivation strategy for the improvement of lipids and carotenoids production by the red yeast *Rhodosporidium toruloides* NCYC 921, *Bioresource Technology*, Apr. 8, 2015, pp. 309-318, vol. 189, Elsevier B.V. https://doi.org/10.1016/j.biortech.2015.04.009.
Yang et al., Recycling microbial lipid production wastes to cultivate oleaginous yeasts, *Bioresource Technology*, Oct. 20, 2014, pp. 91-96, vol. 175, Elsevier B.V. https://doi.org/10.1016/j.biortech.2014.10.020.
Lin et al., Microbial lipid production by *Rhodosporidium toruloides* in a two-stage culture.mode, *Chinese Journal of Biotechnology*, Jul. 25, 2010, pp. 997-1002, vol. 26, No. 7 (English abstract only). XP-002759911.
Polburee et al. Lipid production from biodiesel-derived crude glycerol by *Rhodosporidium fluviale* DMKU-RK253 using temperature shift with high cell density, *Biochemical Engineering Journal*, Apr. 27, 2016, pp. 208-218, vol. 112, Elsevier B.V. DOI:10.1016/j.bej.2016.04.024.
Search Report dated Dec. 18, 2015, by the Finnish Patent and Registration Office in the corresponding Finnish Patent Application No. 20155385.

(Continued)

*Primary Examiner* — Bin Shen
(74) *Attorney, Agent, or Firm* — BUCHANAN INGERSOLL & ROONEY PC

(57) ABSTRACT

The present invention relates to improved methods for producing biosynthetic products in a cascade of bioreactors. In particular the present invention relates to methods and a cascade of bioreactor systems comprising at least two bioreactors and at least one concentration unit.

20 Claims, 10 Drawing Sheets

(56) References Cited

OTHER PUBLICATIONS

Notification of the First Office Action dated Aug. 31, 2020, by the National Intellectual Property Administration of the People's Republic of China in corresponding Chinese Patent Application No. 201680030277.6 and an English translation of the Notification. (22 pages).
Liu et al., "Research and Application of Continuous Cascade System in Fermentation Process," Industrial Microbiology, Sep. 30, 2003, vol. 33, No. 3, pp. 52-56. (5 pages).

* cited by examiner

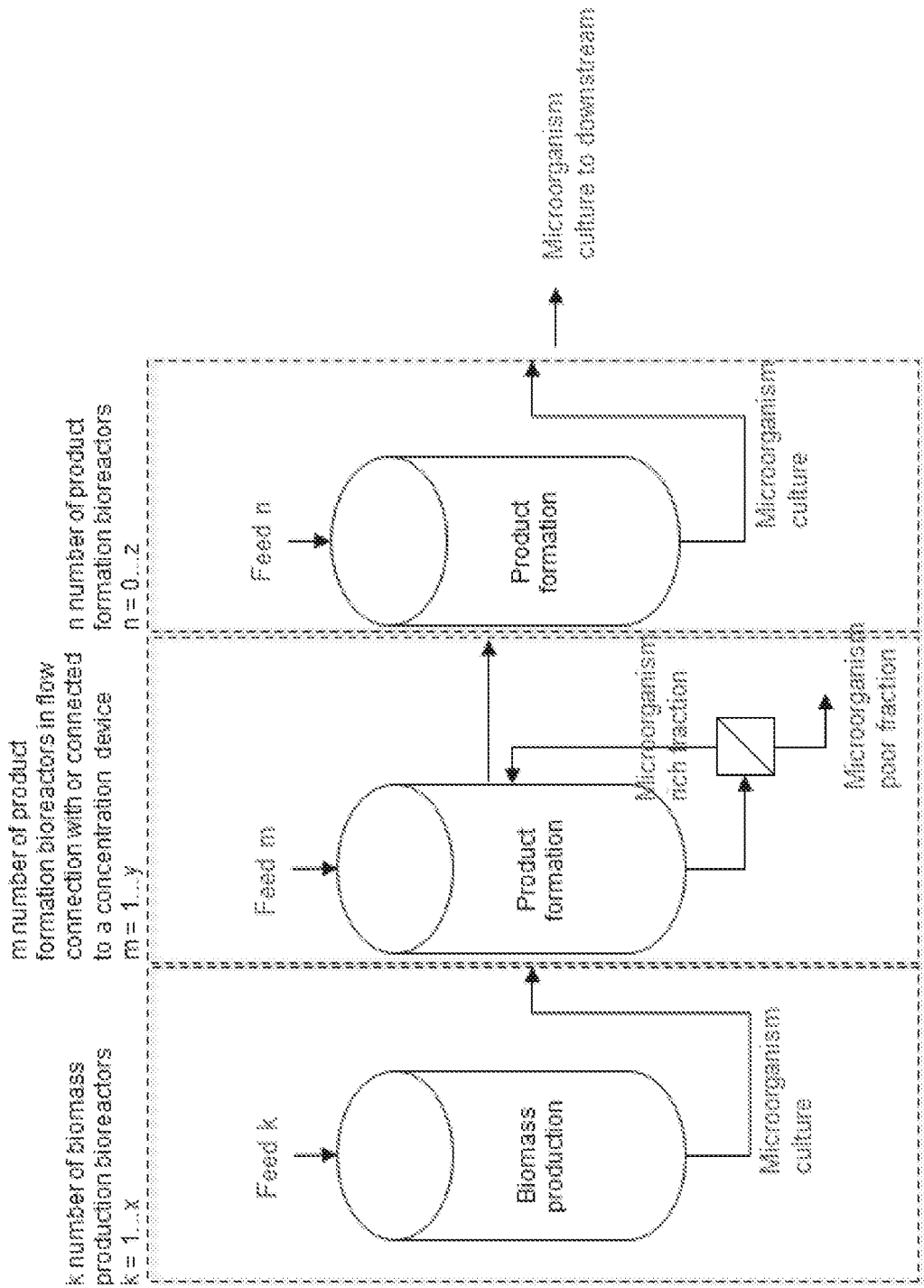
Figure 1. Embodiment of a culturing process for biosynthetic product production.

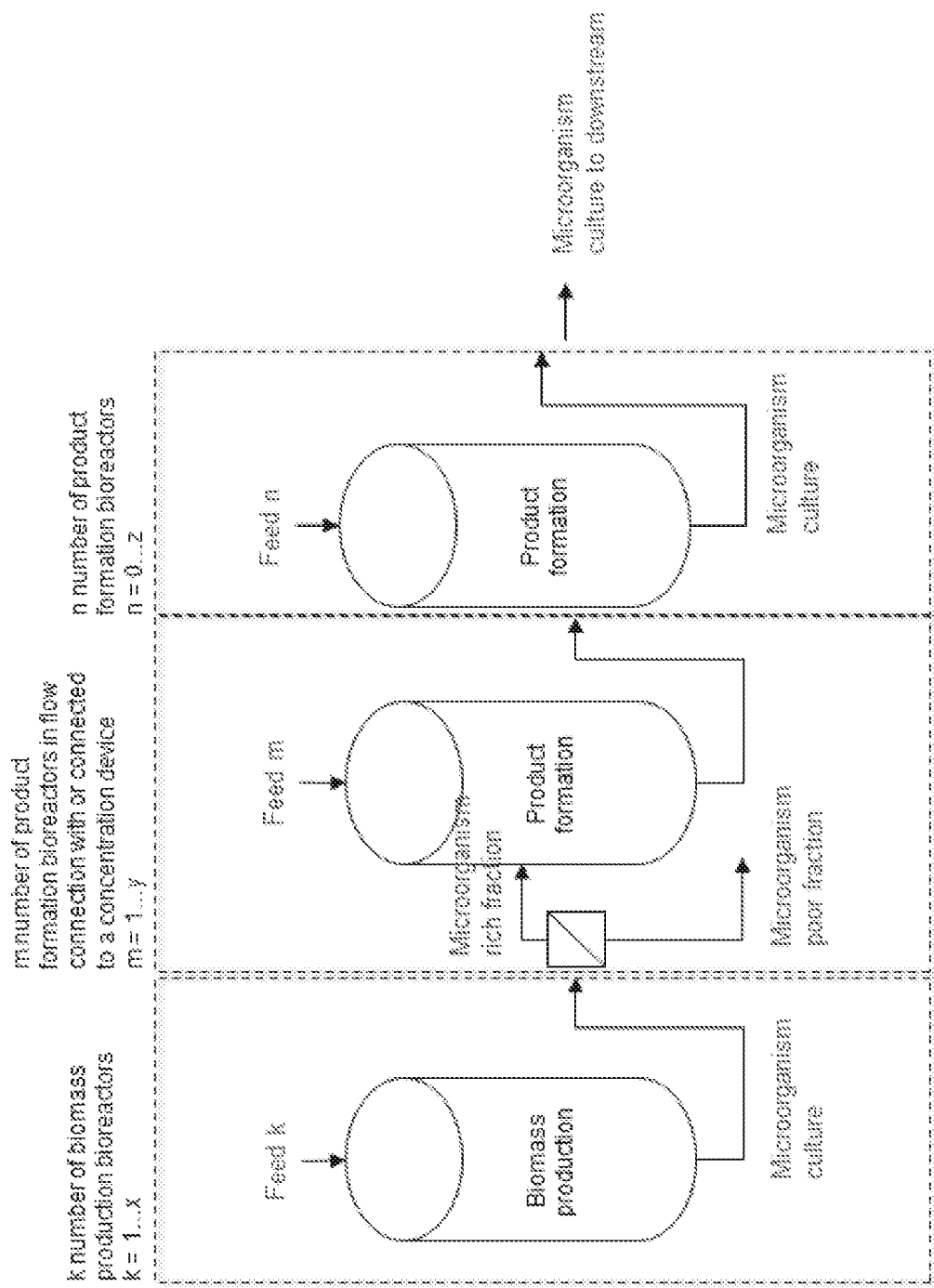
Figure 2. Embodiment of a culturing process for biosynthetic product production.

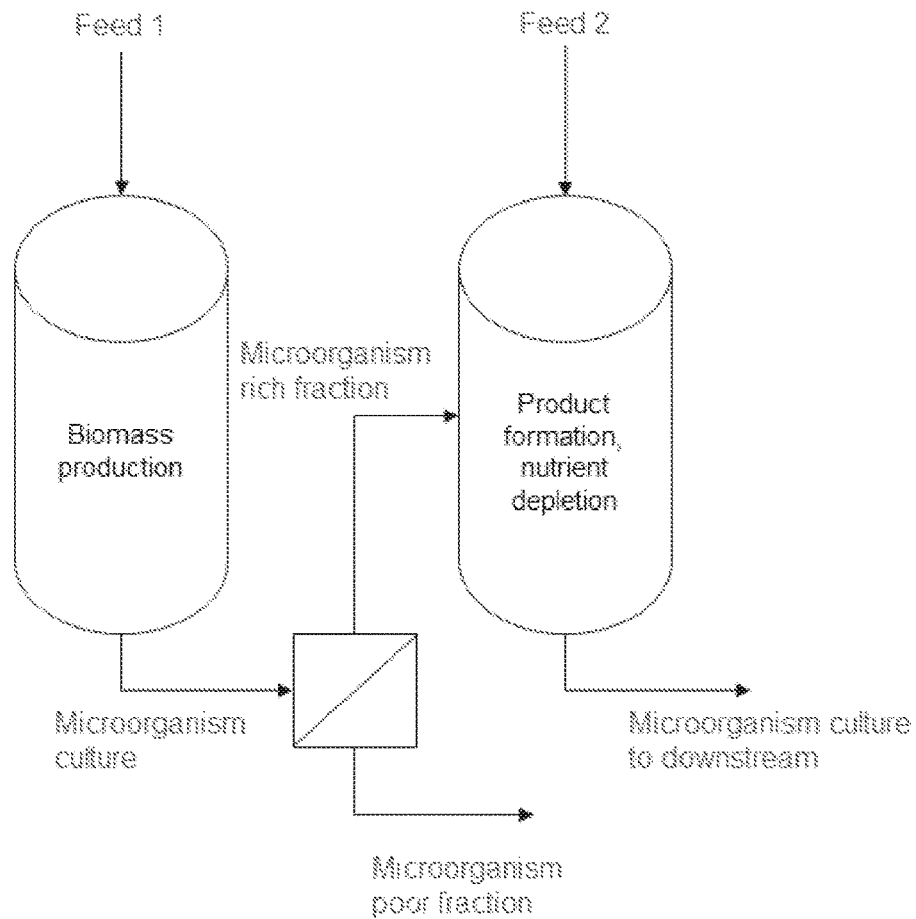
Figure 3. Two-step culturing process for biosynthetic product production with interim concentration, concentration unit configuration 1.

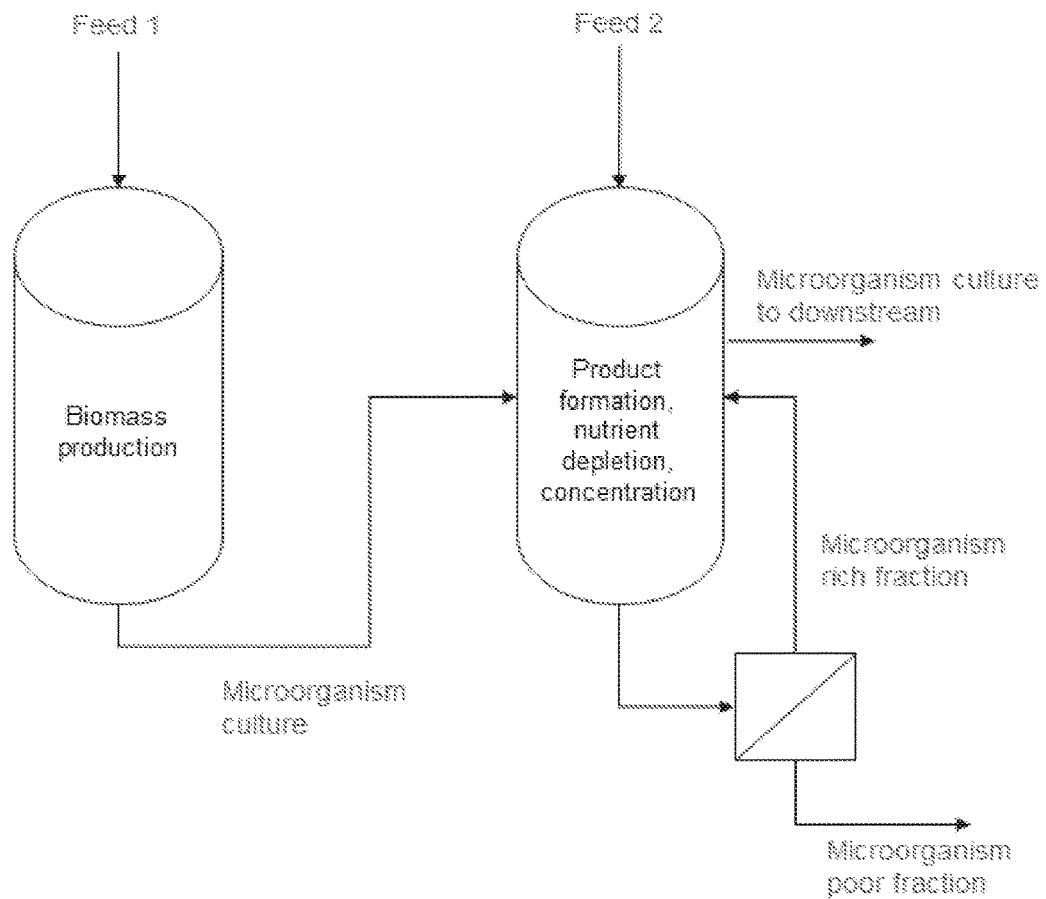
Figure 4. Two step culturing process for biosynthetic product production with interim concentration, concentration unit configuration 2.

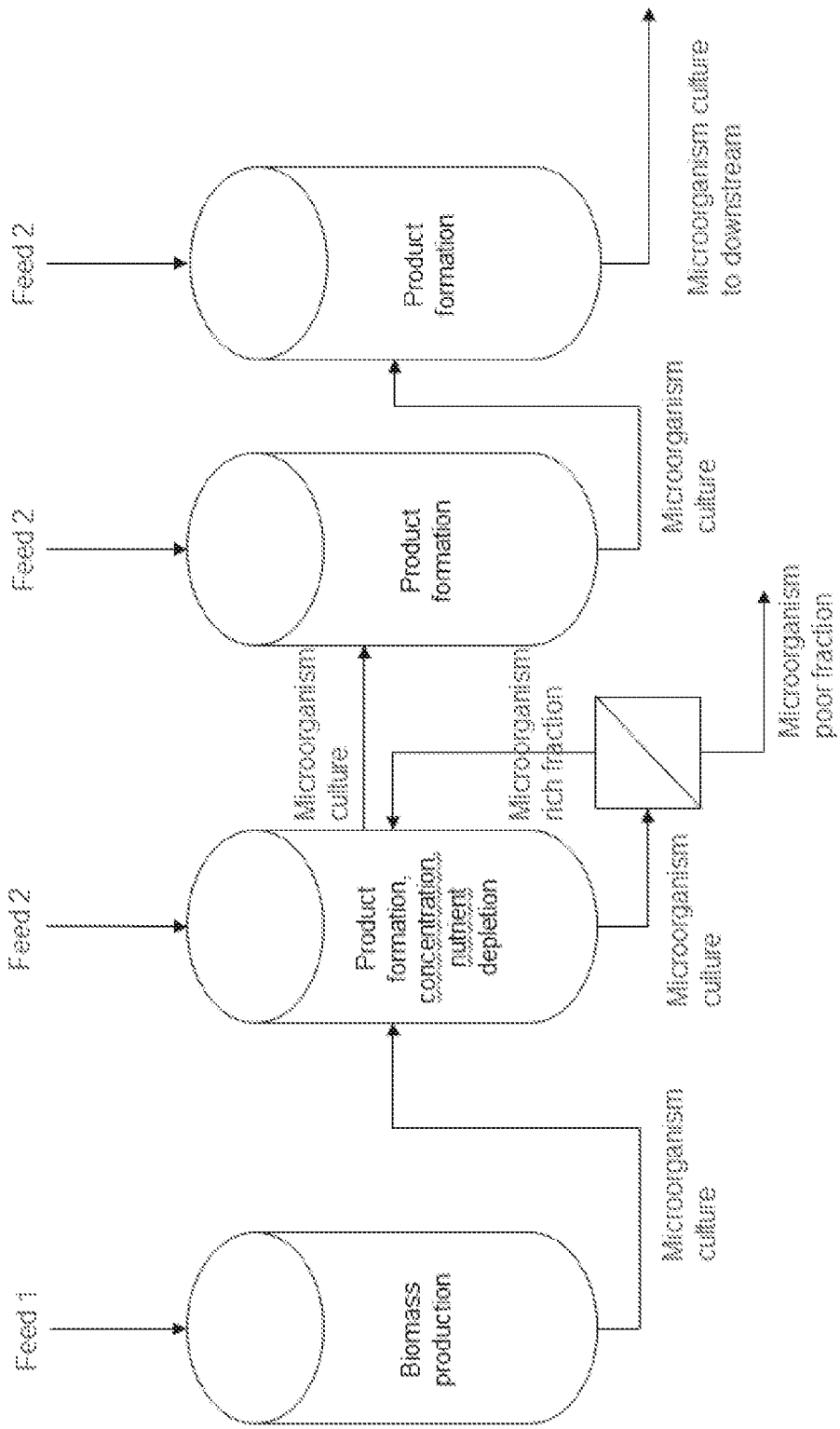
Figure 5. Cascade culturing process for biosynthetic product production with interim concentration.

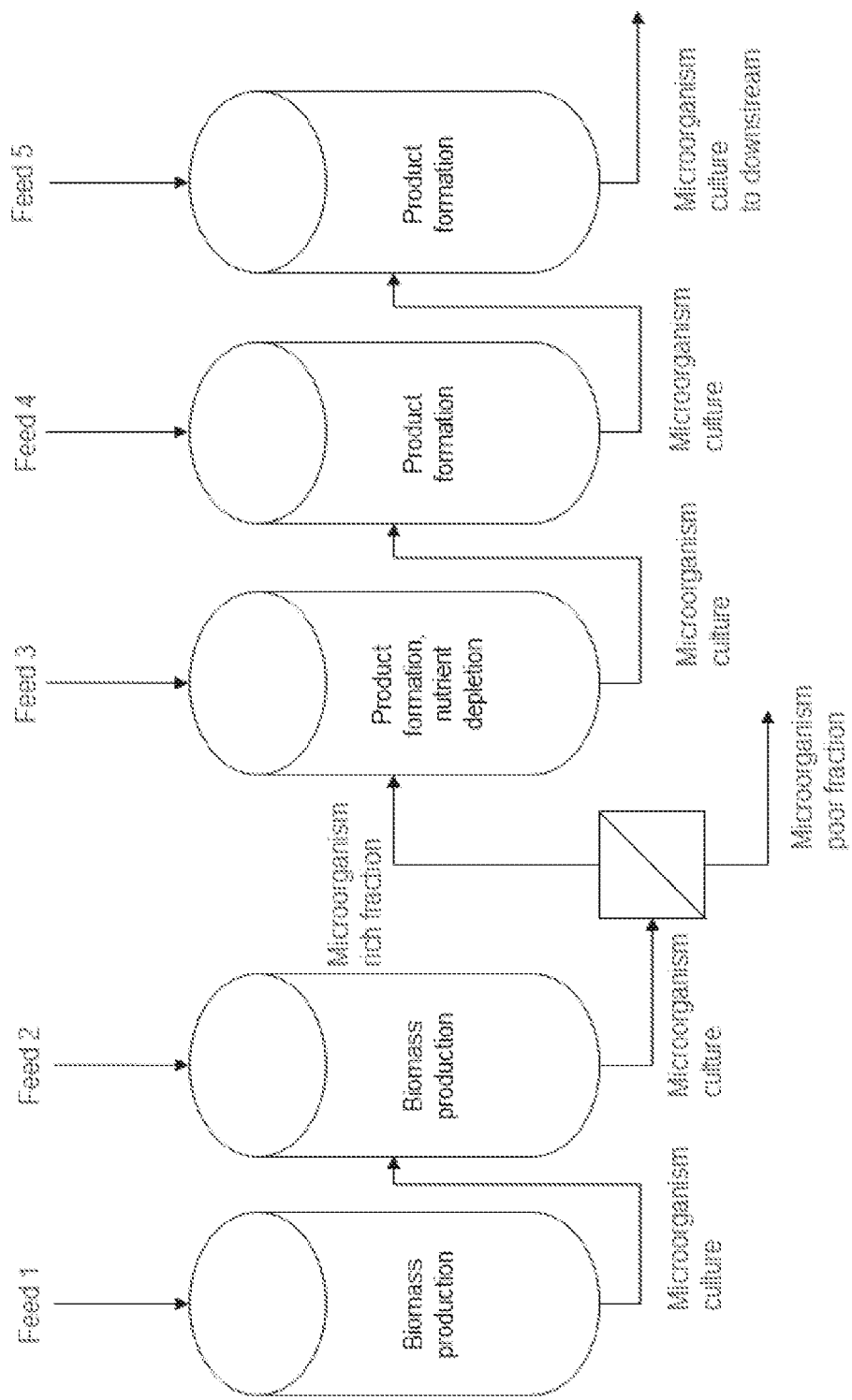
Figure 6. Cascade culturing process for biosynthetic product production with interim concentration with varying feeds.

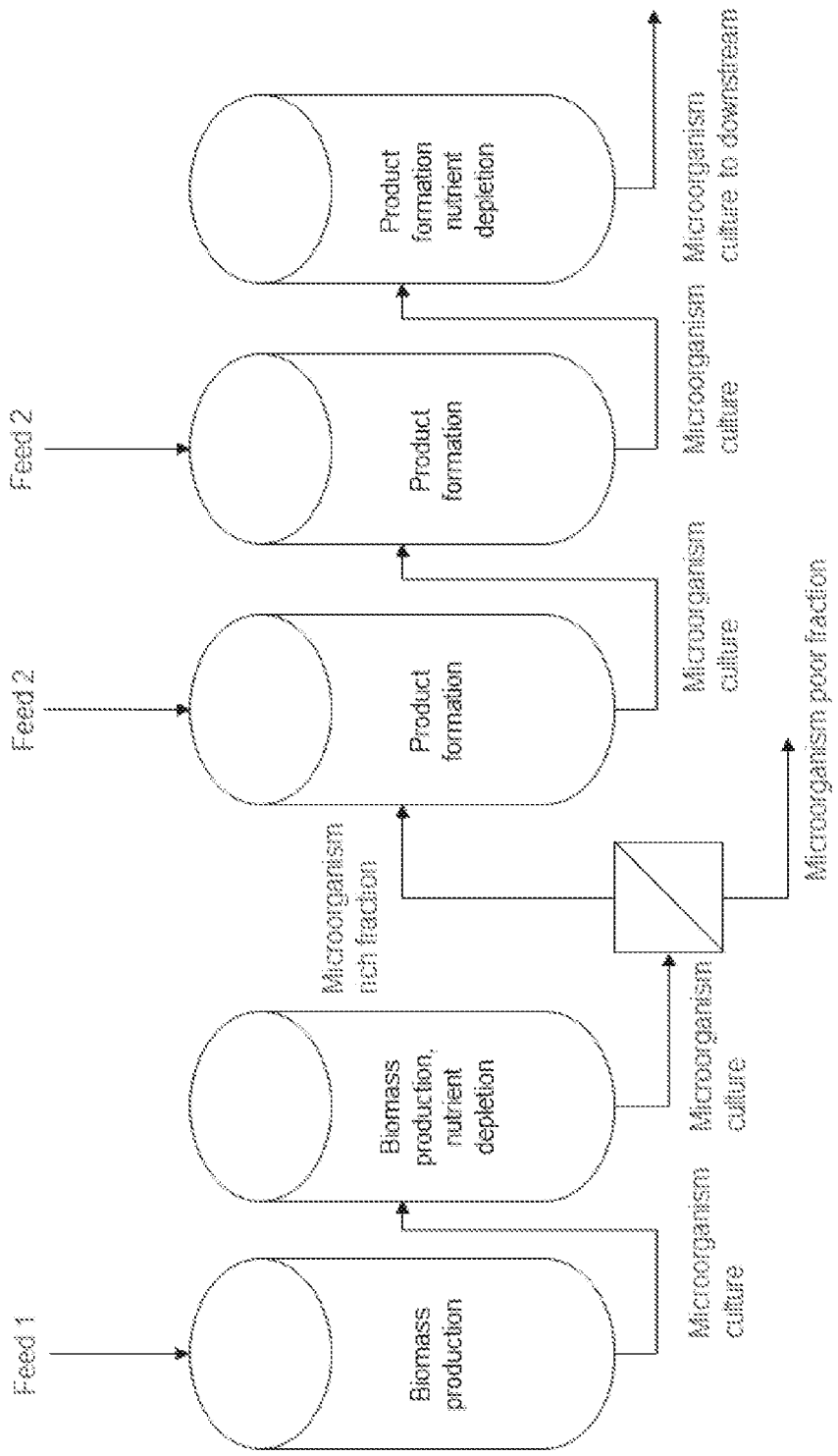
Figure 7. Cascade culturing process for biosynthetic product production with interim cell concentration with bioreactors for nutrient depletion, concentration configuration 1.

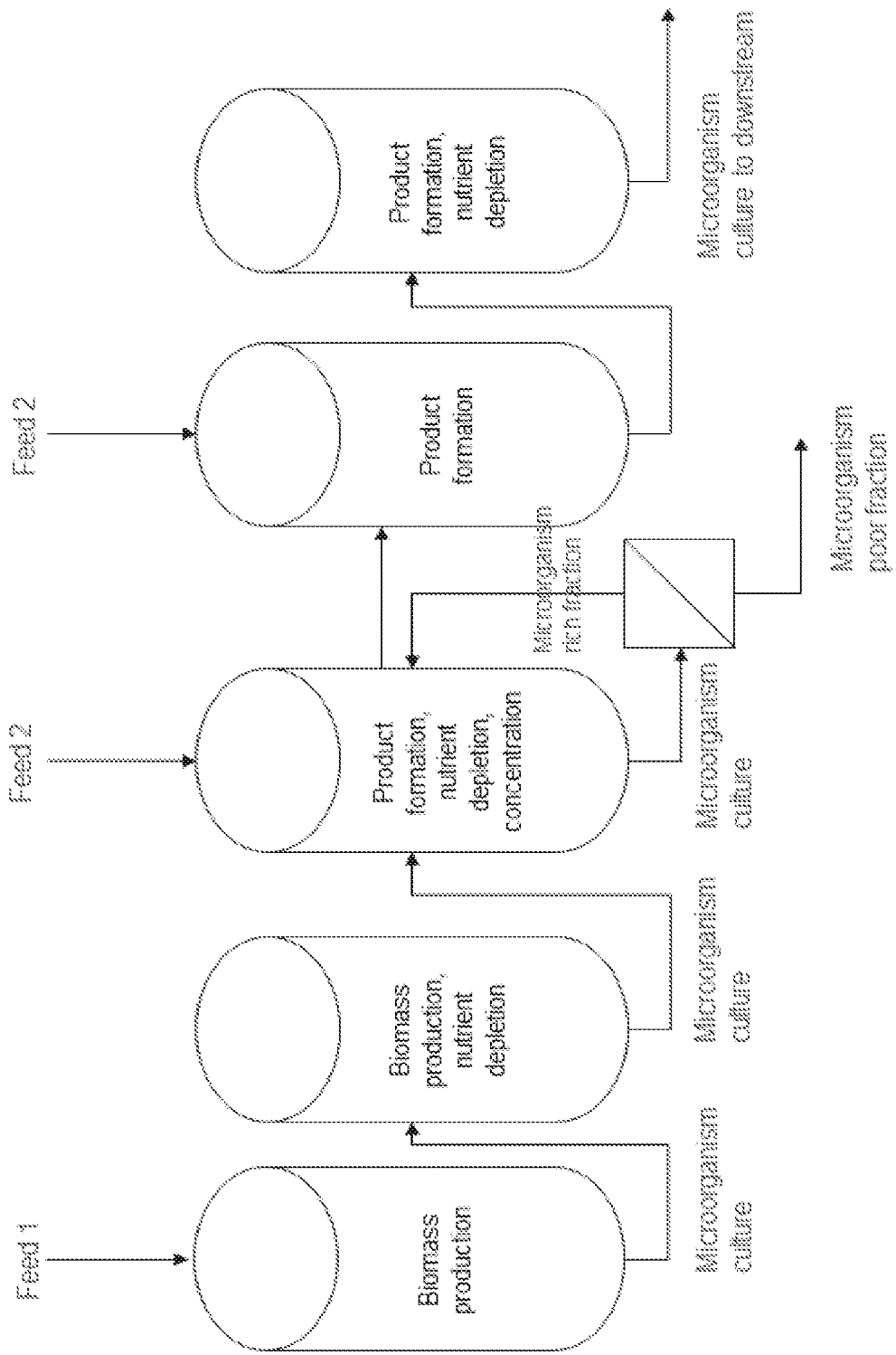
Figure 8. Cascade culturing process for biosynthetic product production with interim cell concentration with bioreactors for nutrient depletion, concentration configuration 2.

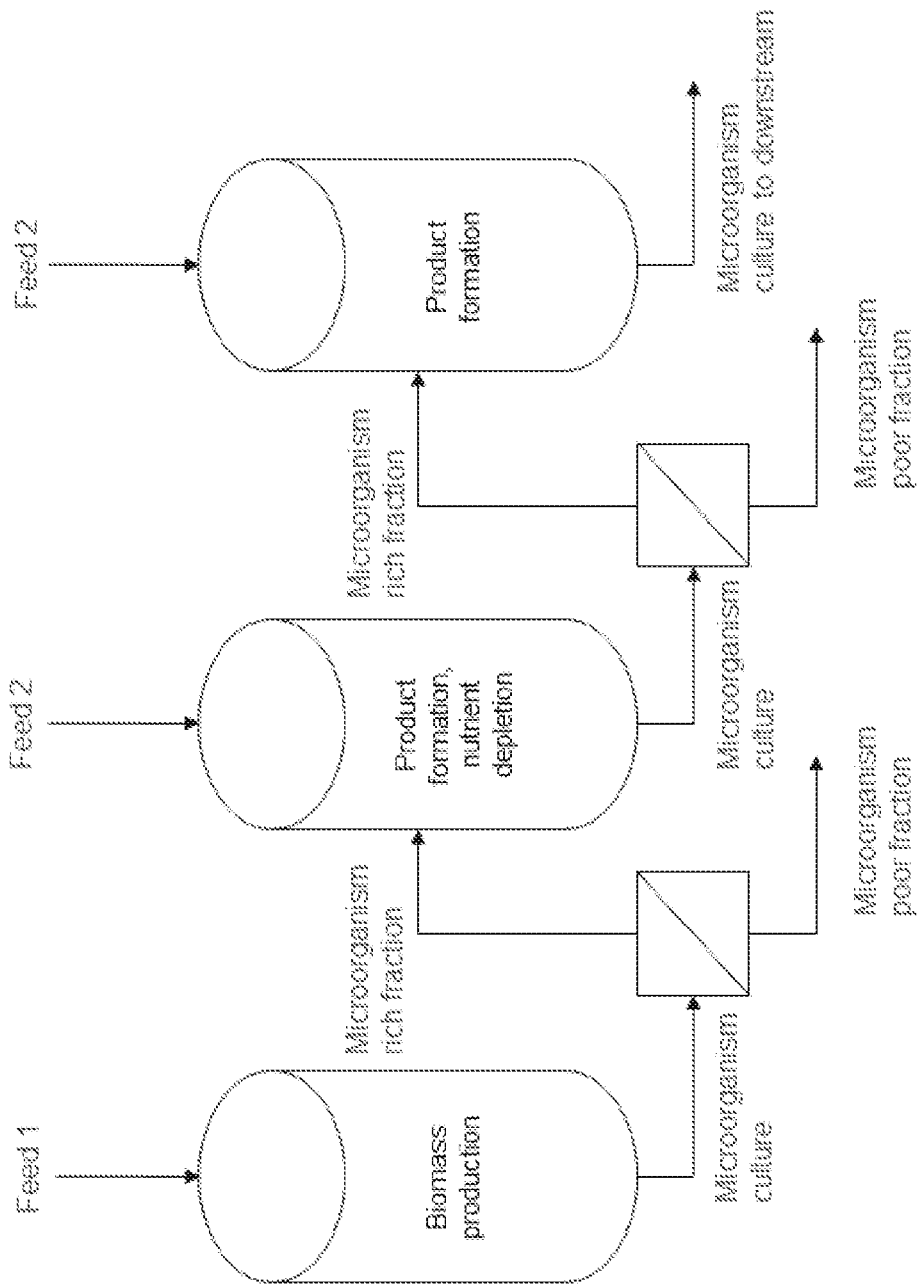
Figure 9. Multiple interim concentration steps, concentration unit configuration 1

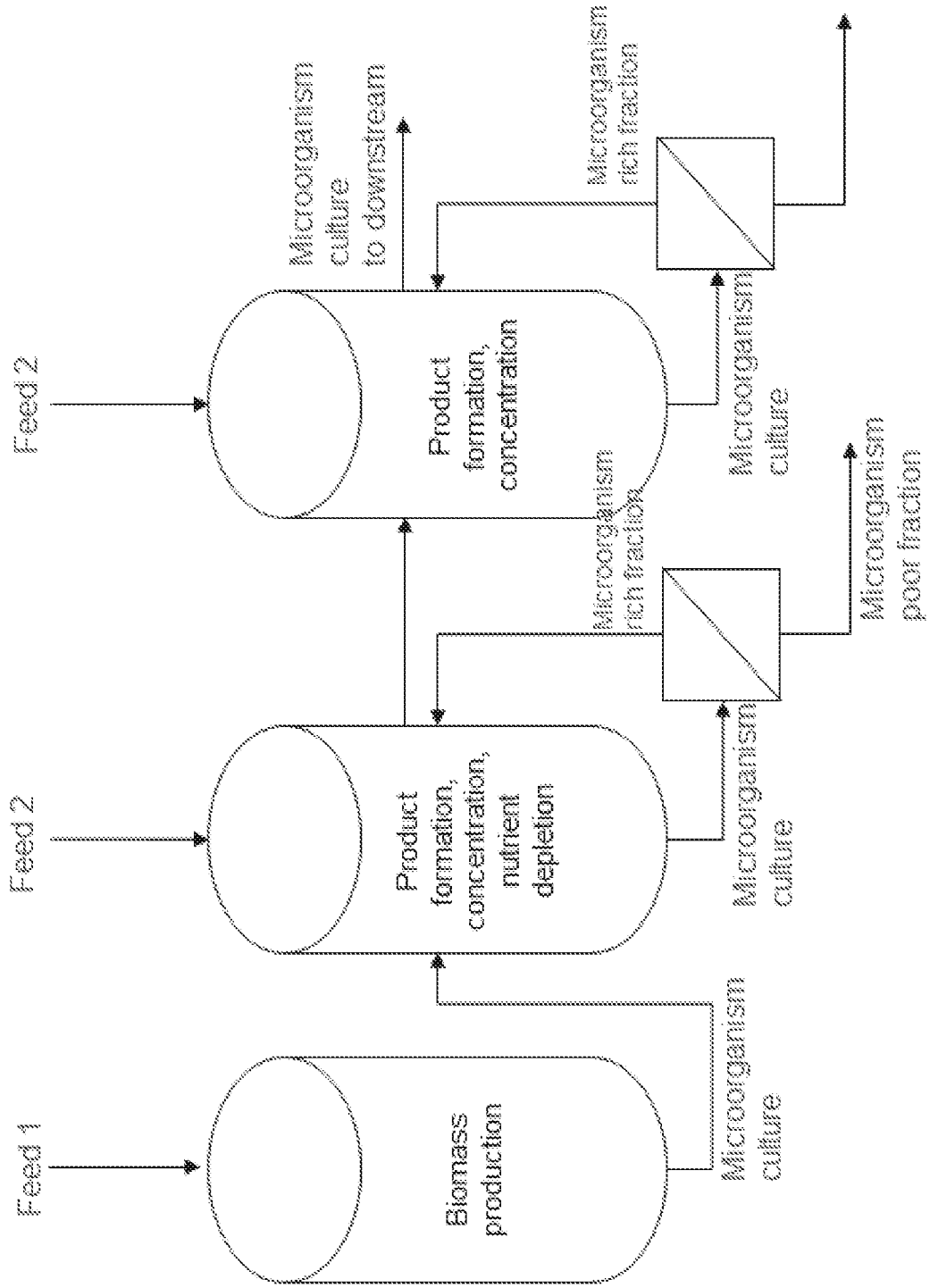
Figure 10. Multiple interim concentration steps, concentration unit configuration 2.

METHODS FOR CONTINUOUS PRODUCTION OF PRODUCTS FROM MICROORGANISMS

FIELD OF THE INVENTION

The present invention relates to the culturing of microorganisms for the production of a biosynthetic product. In particular the present invention relates to a method for producing an intracellular microbial product in a cascade of bioreactors. Specially, the present invention relates to methods and a cascade of bioreactor systems comprising at least two bioreactors and at least one concentration unit.

BACKGROUND OF THE INVENTION

Microorganisms of different kind can be used for production of many different kinds of products, ranging from products they will naturally produce to products they may be manipulated to produce either by genetic engineering or by selected feed supply. Advantageously, certain microorganisms can be grown on cheap waste products to produce important valuable products.

US 2012/0219993 (to Chang et al.) relates to microorganisms for production of intracellular products from volatile fatty acids in multi-stage bioreactor system, wherein the microorganisms are grown in a growth reactor, and subsequently culturing the grown microorganisms in a production reactor of biosynthetic intracellular products. Microorganisms were grown in growth medium, and subsequently cultured in medium comprising growth inhibitory volatile fatty acids as a carbon source for production of intracellular products.

Fermentation, or product formation in reactors of the batch type usually suffers the drawback of low productivity due to low cell concentration. Various attempts have been made to overcome this problem, as well as the problem of end product inhibition when producing organic acids by microbial fermentation or product formation.

U.S. Pat. No. 6,596,521 (to Chang et al.) describes a cell recycle multiple stage continuous fermentor with serially connected fermentors, wherein the concentration of microorganisms in a fermentation reactor is increased by filtering off part of the fermentation media.

There is a need for further methods for producing biosynthetic products, either intracellular or extracellular, as well as improving cost effectiveness in large scale microbial production of biosynthetic products.

SUMMARY OF INVENTION

The present invention was made in view of the prior art described above, and one of the objects of the present invention is to provide improved processes for the production of biosynthetic products in a bioreactor system. Another objective of the present invention is to provide a process, which enables production of the biosynthetic product with high productivity.

The objects of the invention are achieved by a method which is characterized by what is stated in the independent claims. The preferred embodiments of the invention are disclosed in the dependent claims.

The present invention provides a method for producing a biosynthetic product, especially an intracellular product, in a cascade of bioreactors, e.g. serially connected bioreactors, by utilizing at least one biomass production reactor and at least one product formation reactor, said product formation reactor being in flow connection with a concentration device. The method comprises culturing microbial cells (i.e. cells from one or several microorganisms) under optimal conditions for growth, subsequently changing the conditions to allow the cells to enter an effective product formation phase. This process of culturing a microorganism may according to the present invention be performed in a bioreactor system comprising an array of at least two bioreactors (e.g. serially connected) so that cells obtained from culturing said microorganism in one of said bioreactors are concentrated and partly fed into the same or into the subsequent bioreactor in the array of bioreactors.

More specifically the present invention relates to a method for producing a biosynthetic product in a cascade of bioreactors (e.g. serially connected bioreactors), the cascade comprising a bioreactor system for biomass production comprising at least one biomass production reactor, and a bioreactor system for product formation comprising at least one product formation reactor in flow connection with a concentration device, which method comprises:

a) culturing a microorganism in a biomass production bioreactor by feeding the bioreactor with a nutrient rich culture medium allowing efficient growth of biomass;
b) taking at least part of the microorganism culture from the biomass production reactor of step a) and feeding it to a product formation reactor containing nutrient depleted medium optimized for formation of the biosynthetic product;
c) producing the biosynthetic product in the presence of the nutrient depleted product formation medium in the product formation reactor;
wherein the cell mass concentration of the microorganism culture of the product formation reactor is increased by using a concentration device in flow connection with the product formation reactor.

The present invention relates also to use of a cascade of bioreactors (e.g. serially connected bioreactors) comprising at least two or three bioreactors (e.g. serially connected bioreactors) and one or more concentration devices for producing a biosynthetic product, wherein one or more concentration devices are in flow connection with a product formation reactor and arranged between and in line with two bioreactors.

The inventors of the present invention have found that by concentrating at least part of the cells obtained from the biomass production reactor or the product formation reactor in a concentration device and by at least partly feeding the obtained micro-organism rich fraction into the same or into the subsequent product formation bioreactor in the cascade of bioreactors (e.g. serially connected bioreactors), the productivity of the biosynthetic production process can be significantly improved.

BRIEF DESCRIPTION OF DRAWINGS

FIG. 1 presents an embodiment of a culturing process for biosynthetic product formation, wherein is presented a cascade of bioreactors with a first set of parallel bioreactors for biomass production comprising k number of biomass production reactors, wherein k is between 1 and x, followed by a next step comprising m number of parallel product formation reactors, wherein m is between 1 and x. The m product formation reactors in this step are in flow connection with or connected to a concentration device for obtaining a microorganism rich fraction of the microorganism culture taken from the product formation bioreactor. The microorganism rich fraction is recycled to the same bioreactor, while the microorganism poor fraction is discarded from the process. The first series of product formation reactors are followed by a next step comprising n number of product formation reactors, wherein n is between 1 and x. Feeds: Feed k: k=number of the biomass production bioreactor 1 . . . x, Feed m: m=number of the product formation bioreactor in flow connection or connected with a concentration device 1 . . . y, Feed n: n=number of the product formation bioreactor 1 . . . z. Individual feeds, k (1 . . . x), m (1 . . . y) and n (1 . . . z), can be of the same composition or some of the feeds are of the same composition or all the feeds are of different compositions.

FIG. 2 presents an embodiment of a culturing process for biosynthetic product formation, which is similar to that presented in FIG. 1, but with the difference that the concentration device is positioned between the biomass production reactor and the product formation reactor. This has the effect that while the concentration step still leads to increased cell concentration in the m number of product formation reactors, the composition of the microorganism culture in the m number of production reactors will be less influenced by the contents of the biomass production reactor, as the microorganism poor fraction and the microorganism rich fraction from these bioreactors is separated before entering the m number of product formation reactors, whereby only part of the media from the biomass production reactors will enter the product formation reactors. Feeds: Feed k: k=number of the biomass production bioreactor 1 . . . x, Feed m: m=number of the product formation bioreactor in flow connection or connected with a concentration device 1 . . . y, Feed n: n=number of the product formation bioreactor 1 . . . z. Individual feeds, k (1 . . . x), m (1 . . . y) and n (1 . . . z), can be of the same composition or some of the feeds are of the same composition or all the feeds are of different compositions.

FIG. 3 shows an embodiment of two-step culturing process for biosynthetic product formation with interim concentration, concentration unit configuration 1.

FIG. 4 shows an embodiment of two-step culturing process for biosynthetic product formation with interim concentration, concentration unit configuration 2.

FIG. 5 shows an embodiment of cascade culturing process for biosynthetic product formation with interim concentration.

FIG. 6 shows an embodiment of cascade culturing process for biosynthetic product formation with interim concentration and with varying feeds.

FIG. 7 shows an embodiment of cascade culturing process for biosynthetic product formation with interim cell concentration with fermentors for nutrient depletion, concentration configuration 1.

FIG. 8 shows an embodiment of cascade culturing process for biosynthetic product formation with interim cell concentration with fermentors for nutrient depletion, concentration configuration 2.

FIG. 9 shows an embodiment of a culturing process for biosynthetic product formation with multiple interim concentration steps, concentration unit configuration 1.

FIG. 10 shows an embodiment of a culturing process for biosynthetic product formation with multiple interim concentration steps, concentration unit configuration 2.

DETAILED DESCRIPTION OF THE INVENTION

In describing the embodiments of the invention specific terminology will be resorted to for the sake of clarity. However, the invention is not intended to be limited to the specific terms so selected, and it is understood that each specific term includes all technical equivalents which operate in a similar manner to accomplish a similar purpose.

Definitions

The term "bioreactor" as used herein refers the reactors in which microorganisms are grown or in which they produce biosynthetic products. Different types of bioreactors providing different advantages with regard to optimising culture conditions may be used. In one embodiment of the invention air-lift bioreactors are used in the cascade. According to another embodiment of the invention both stirred tank bioreactors and air-lift bioreactors may be used in the cascade. According to another embodiment of the invention only stirred tank bioreactors are used in the cascade.

As used herein terms "reactor" and "bioreactor" are used interchangeably.

The term "Product", also referred to as "biosynthetic product", as used herein refers to biosynthetic products synthesized via natural and/or genetically modified metabolism including both intra and extra cellular products that can be either primary or secondary metabolites.

The term "lipid" refers to a fatty substance, whose molecule generally contains, as a part, an aliphatic hydrocarbon chain, which dissolves in nonpolar organic solvents but is poorly soluble in water. Lipids are an essential group of large molecules in living cells. Lipids are, for example, long chain diacids, hydroxyl fatty acids, long chain diols, lipids, fats, oils, waxes, farnesene type products, wax esters, sterols, terpenoids, isoprenoids, carotenoids, polyhydroxyalkanoates, nucleic acids, fatty acids, fatty acid derivates, fatty alcohols, fatty aldehydes, fatty acid esters, fatty amines, medium and long chain dicarboxylic acids, epoxy fatty acids, long chain diols and polyols, phospholipids, glycolipids, sphingolipids and acylglycerols, such as triacylglycerols, diacylglycerols, or monoacylglycerols. The terms "lipid", "oil" and "fat" are used in this description synonymously. The term "acyglycerol" refers to an ester of glycerol and fatty acids. Acylglycerols occur naturally as fats and fatty oils. Examples of acylglycerols include triacylglycerols (TAGs, triglycerides), diacylglycerols (diglycerides) and monoacylglycerols (monoglycerides).

The term "microbial lipid" or "microbial oil" refers to a lipid produced, transformed or modified by a microorganism. The term "microbial lipid" encompasses the category "single cell oil".

In productivity (g/(l*h)) the l is the bioreactor volume measured in liters and g refers to mass of product in grams.

The term "cell growth curve" refers to which growth state the microbial cells are at, e.g. are they in the exponential growth phase or in late exponential phase or in the stationary phase. The status will indicate which conditions regarding nutrition, temperature and aeration are optimal for the cells at the time. When referring to "optimization of process conditions in individual bioreactors according to cell growth curve" it is meant that it may be beneficial to amend culturing conditions in order to shift cells into other conditions, in order to make the cells enter the next phase, such as going from exponential growth to late exponential growth phase.

The term "cell separation step" or "separation" is a cell concentration step, where part of the microorganism culture is separated from another part which in consequence will comprise an increased density of cells as compared to before the separation step. Cell concentration may be achieved by different means, such as for example filtration, centrifugation, decanting, settling, flocculation and/or flotation (e.g. as unit operation). Many different types of cell concentration devices may be used in the present invention, and the skilled person will be able to select suitable means.

The term "concentration device" refers to any device, which is used for obtaining a microorganism rich fraction of the microorganism culture. Optionally, in addition to a microorganism rich fraction also microorganism poor fraction is obtained. Cell concentration may be achieved by different means, such as for example filtration, centrifugation or by decanting. Many different types of cell concentration devices may be used in the present invention, and the skilled person will be able to select suitable means. "A concentration device being in flow connection with the product formation reactor" refers to a situation, wherein flow connection is for delivering microorganism culture to said concentration device or delivering cell mass from said concentration device to the product formation reactor.

The term "increased cell mass concentration of the microorganism culture" refers to an increased biomass concentration of the microorganism culture compared to the microorganism culture before the separation step (as measured in weight % g/l, cfu (colony forming units), or by optical density).

The term "product formation curve" refers to the different phases of product formation. Cell culturing or fermentation conditions may be different during different phases, why change of media to induce nutrient starvation may be beneficial, in order to e.g. induce utilization of non-preferred nutrients such as sugars. Having e.g. certain nutrient or aeration conditions may keep cells in a product formation mode.

The term "biomass production reactor", refers to a bioreactor in which temperature, pH, nutrient and aeration conditions are such that cell division is optimized. The main purpose of a biomass production reactor is to produce biomass. In case of anaerobic growth no aeration of the bioreactor is performed.

The term "product formation reactor", refers to a bioreactor in which nutrient, temperature, pH and aeration conditions are optimized for product formation. In case of anaerobic growth no aeration of the bioreactor is performed.

The term "aerobic" refers to e.g. cellular culturing under aerobic conditions, where a microorganism can generate energy in the form of ATP by oxidative respiration. The method of the present invention may be run under aerobic, anaerobic or micro aerobic conditions.

The term "anaerobic" refers to e.g. cellular culturing or fermentation without oxygen. An anaerobic fermentation process is herein defined as a fermentation process run in the absence of oxygen or in which substantially no oxygen is consumed, and wherein organic molecules serve as both electron donor and electron acceptors.

The term "micro aerobic" refers to oxygen-limited conditions i.e. an environment in which the concentration of oxygen is less than in air. An oxygen-limited method is a method in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used.

The term "production" refers to the cells metabolic synthesis of microbial products or biosynthetic products, such as microbial transformation of compounds (e.g. fatty acids to diacids) or by de novo synthesis.

As used herein "intracellular products" refers to any products produced by microorganisms and remaining inside the cell. "Intracellular products" is used in contrast to "extracellular products".

As used herein "extracellular products" refers to any products produced by microorganisms and moving or transported outside the cell, e.g. outside the plasma membrane.

The term "Secondary metabolite" as used herein refers to a product produced intra or extra cellularly by a microorganism near the end of the growth phase or during the stationary growth phase.

The term "Primary metabolite" as used herein, refers to a product produced intra or extra cellularly by a microorganism during the growth phase including metabolites involved in growth, development and reproduction that typically are energy metabolism related products such as ethanol and lactic acid are primary metabolites.

The term "Growth" refers to an increase in cell number or an increase in microbial mass, also referred to as "growth phase".

The term "Exponential growth" as used herein refers to growth of a micro-organism where the cell number doubles within a fixed time period.

The term "Exponential growth phase" as used herein refers to a period of the growth cycle of a population in which growth increases at an exponential rate. Also referred to as exponential phase.

The term "Stationary growth phase" or "stationary phase" as used herein refers to the period during the growth cycle of a microbial population in which growth ceases meaning no net increase or decrease in the cell number or microbial mass. In connection to the present invention, stationary growth phase is also used to refer to the phase during the growth cycle of a microbial population in which slow, but no more exponential, net increase in cell number or microbial mass occurs, also referred to as "late exponential growth phase" or "late stage exponential growth phase" or "early stationary growth phase". Typically, the stationary growth phase is reached when some growth nutrient becomes growth limiting or accumulation of inhibitory metabolic products inhibits cell growth. In the stationary growth phase, many cell functions may continue, for example energy metabolism and some biosynthetic processes.

The term "Resting cells" as used herein refers to dormant cells, spores or other microbial resting, non-growing, cell forms. In connection to this invention, although no growth occurs in resting cells, some metabolic and/or biosynthetic processes producing biosynthetic product may occur.

The term "product formation phase" may be defined as a phase, in which typically at least 80% of the end product is formed.

The term "media" or "culturing media" refers to the different types of media used in the present invention. Media or culturing media is suitable for e.g. biomass production or product formation. In some embodiments of the invention media for product formation may be the same as the media for biomass production.

The term "microorganism rich fraction" or "cell rich fraction" is the fraction of the microorganism culture which after separation, i.e. a cell separation step or a concentration step, comprises an increased biomass concentration compared to the microorganism culture before the separation step.

As used herein "microbial" and "microorganism" are used interchangeably.

The term "culturing" as used herein, refers to the process of growing the microbial cells under optimal conditions for microbial culture. In one embodiment of the invention "culturing" refers to any method step of the present invention e.g. during the different phases wherein the microbial cells produce biomass or the biosynthetic product of the present invention.

The term "culturing conditions" as used herein, refers to all the conditions which influence the optimal performance of the microbial cells in either growth or product formation or in their transition between the different phases of growth or product formation. As an example, "culturing conditions" include any aerobic, anaerobic or micro aerobic conditions.

The term "microorganism culture" refers to a culture comprising microorganisms and media for culturing the microorganism cells (e.g. biomass production or product formation). In some embodiments of the invention the culture also comprises a biosynthetic product.

The term "fermentation" as used herein, refers to anaerobic fermentation of microbial cells for biosynthetic product formation.

The term "cascade" or "cascade process" refers to a process of culturing microbial cells for production of biosynthetic products. The process is performed in a set (e.g. cascade) of bioreactors, where the microbial cells may be moved between bioreactors, in order to allow for changes of the culturing or fermentation conditions for the cells according to the different steps of the of the process. The term cascade refers to the flow of cells through the bioreactor system allowing for a continuous or fed batch culturing and product formation process.

The term "Single cell oil" as used herein refers to a fatty substance, whose molecule generally contains, as a part, an aliphatic hydrocarbon chain, which dissolves in nonpolar organic solvents but is poorly soluble in water. Single cell oils are an essential group of large molecules in living cells. Single cell oils are, for example, lipids, fats, waxes, wax esters, sterols, terpenoids, isoprenoids, carotenoids, polyhydroxyalkanoates, nucleic acids, fatty acids, fatty acid derivates, fatty alcohols, fatty aldehydes, fatty acid esters, fatty amines, medium and long chain dicarboxylic acids, epoxy fatty acids, long chain diols and polyols, phospholipids, glycolipids, sphingolipids and acylglycerols, such as triacylglycerols, diacylglycerols, or monoacylglycerols. In connection to this invention single cell oil refers to both intra and extra cellular single cell oil products produced via de novo synthesis as well as by microbial transformation of culture medium components. In connection to this invention "lipid" and "microbial oil" are used as synonyms for single cell oil.

The term "microorganism" encompasses any microorganism capable of producing a biosynthetic product, e.g. a fungus, such as a filamentous fungus or yeast, a heterotrophic algae, a bacterium or an archaebacterium. One or several different microorganisms may be utilized in the present invention.

The microorganism for use in the processes of the present invention may be any one of:

Filamentous fungi: *Penicillium, Aspergillus, Trichoderma, Rhizopus, Humicola, Zycomycota, Ascomycota, Mucor, Mortierella*, Species such as *Penicillium chrysogenum, Trichoderma reesei, Aspergillus niger* or *Aspergillus terreus*

Yeasts: *Saccharomyces, Schizosaccharomyces, Candida, Pichia, Rhodosporidium, Rhodotorula, Cryptococcus*, Species such as *Candida tropicalis, Saccharomyces cerevisiae, Pichia pastoris, Pichia stipilis, Schizosaccharomyces pombe, Rhodosporidium toruloides* or *Rhodosporidium fluviale* Bacteria: *Escherichia, Bacillus, Brevibacterium, Streptomyces, Actinomyces, Arthrobacter, Alcaligenes, Nocardia, Corynebacterium, Cupriviadus, Zymomonas, Clostridium, Streptococcus, Rhodococcus, Ralstonia, Lactobacillus*, Species such as *Escherichia coli, Bacillus subtilis, Bacillus licheniformis, Brevibacterium flavum, Corynebacterium glutamicum, Cupriviadus necator (Ralstonia eutropha), Rhodococcus opacus, Clostridium ljungdahlii, Clostridium autoethanogenurn, Clostridium butyricum, Clostridium acetobutylicum, Clostridium beijerinckii.*

In non-limiting example, microalgae suitable for the present invention include Chlorophyceae (recoiling algae), Dinophyceae (dinoflagellates), Prymnesiophyceae (haptophyte algae), Pavlovophyceae, Chrysophyceae (golden-brown algae), Diatomophyceae (diatoms), Eustigmatophyceae, Rhapidophyceae, Euglenophyceae, Pedinophyceae, Prasinophyceae and Chlorophyceae. More specifically, microalgae may be selected from the group consisting of *Dunaliella, Chlorella, Botryococcus, Haematococcus, Chlamydomas, Crypthecodinium, Isochlysis, Pleurochlysis, Pavlova, Phaeodactylum, Prototheca, Schizochytrium, Skeletonema, Chaetoceros, Nitzschia, Nannochloropsis, Tetraselmis* and *Synechocystis*.

In some embodiments, microorganisms capable of producing lipids or enzymes are used. Such microorganisms are typically a fungus, in particular a filamentous fungus (mold) or a yeast, microalga or bacterium. Lipid producing molds, dimorphic molds and filamentous fungi comprise, in non-limiting example, those in the genera *Absidia, Aspergillus, Blakeslea, Chaetomium, Cladosporium, Claviceps, Clodosporidium, Cunninghamella, Emericella, Entomophthora, Fusarium, Gibberella, Glomus, Humicola, Mucor, Mortierella, Paecilomyces, Penicillium, Puccia, Pythium, Rhizopus, Saprolegnia, Trichoderma, Umbelopsis, Ustilago* and *Zygorhynchus*, such as molds of the genus *Absidia spinosa, Aspergillus*, for example *A. ficheri, A. flavus, A. nidulans, A. niger, A. ochraceus, A. oryzae, A. sojae* and *A. terreus, Blakeslea trispora, Chaetomium globosum, Cladosporidium herbarum, Claviceps purpurea*, molds of the genus *Cunninghamella*, for example *C. echinulata, C. japonica* and *C. elegans, Entomophthora coronata, Fusarium bulbigenurn, Fusarium graminearum, Fusarium* sp., *Gibberella fujikuroi, Glomus caledonius, Humicola lanuginosa, Humicola grisea*, molds of the genus *Mucor*, for example *M. circinelloides, M. plumbeus* and *M. rouxii*, molds of the genus *Mortierella*, for example *M. isabellina, M. alpina* and *M. ramanniana*, molds of the genus *Penicillium*, for example *P. javanicum, P. lilacinurn, P. spinulosum* and *P. soppii, Paecilomyces lilacinus, Puccia coronata, Pythium ultimum, Pythium irregulare, Rhizopus arrhizus, Rhizopus delemar, Rhizopus oryzae, Ustilago zeae, Ustilago maydis, Zygorhynchus moelleri*, as well as *Malbranchea pulchella, Myrothecium* sp., *Sclerotium bataticola, Pellicularia practicola, Sphacelothea reiliana, Tyloposporidium ehren bergii, Achyla americana, Lepista nuda, Tilletia controversa, Cronartium fusiform. Umbelopsis isabellina* and *Umbelopsis ramanniana, Umbelopsis vinaceae* and *Umbelopsis angularis*.

Yeasts from the genera, but not limited to *Cryptococcus, Trichosporon, Apiotrichum, Hansenula, Lipomyces, Rhodosporidium, Candida, Yarrowia, Rhodotorula, Sporobolomyces, Sporidiobolus, Trichosporon, Torulopsis, Waltomyces, Endomyces, Galactomyces, Pichia* or *Cryptococcus*, such as *Cryptococcus curvatus, Cryptococcus albidus, C. terricolus, Trichosproron cutaneum, Lipomyces starkeyi, L. lipofera, Rhodosporidium toruloides, Candida curvata, Yarrowia lipolytica, Rhodotorula glutinis, Rhodosporidium fluviale, Rhodosporidium diobovatum, Rhodosporidium krato-*

*chvilovae, Sporobolomyces, Candida, Candida* sp. 107, *Lipomyces* sp. 33, *Rhodotorula gracilis, Trichosporon pullulans* or *T. fermentans* can also be used.

Producing a Biosynthetic Product

This invention describes a novel, cost efficient cultivation process for production of biosynthetic products, especially intracellular products, using cultured microorganisms.

The microorganisms may produce the biosynthetic product with or without being induced to do so, in example via induction by environmental conditions, such as presence or absence of certain nutritional factors, such as carbon source or vitamins or other factors in the media, or by changes in temperature, pH, dissolved oxygen or other. Additionally, in some embodiments the microorganisms may be genetically modified to be able to produce the biosynthetic product, in example by introduction of a recombinant gene capable of encoding the desired biosynthetic product, or wherein the recombinant gene expresses an enzyme which is capable of catalysing the synthesis of the desired biosynthetic product. Recombinant DNA techniques for creating genetically modified microorganisms are well known in the art, such as in Sambrook and Russel (2001 "Molecular Cloning: A laboratory Manual" ($3^{rd}$ edition), Cold Spring Harbor Laboratory Press.

The cultivation process is based on the use of a bioreactor cascade comprising at least two bioreactors (i.e. the biomass production bioreactor and the product formation bioreactor) connected in series and one or more cell concentration devices arranged between and in line with two serially connected bioreactors. The cell concentration device may also be arranged after the last bioreactor, or in connection to a bioreactor.

The bioreactor cascade comprising of at least two serial connected bioreactors may specifically be operated as a cascade process. The cascade process is easily adaptable when different types of feeds are needed in different process phases, such as growth and production phases. Different feeds are required e.g. the cultivation of biomass requires nutrient rich feed and the product formation phase requires a nutrient deficient feed for example to achieve nutrient starvation. Product formation may also be induced by other changes in cultivation conditions, such as pH, temperature, aeration conditions or addition of an inducing chemical. Cultivation of biomass may also be sugar dependent while the product formation phase may require a different kind of feed, e.g. oils and fats in the feed.

The production of a biosynthetic product can generally be presented to comprise a two phases: a growth phase in which the amount of biomass increases and a production phase, in which major part of the biosynthetic product is generated. The growth phase may be conducted in one or several bioreactors (growth reactor(s)) and the production phase can be conducted in one or several bioreactors. A culturing medium may be fed into the biomass production bioreactor and medium for product formation may be fed to the product formation reactor. Alternatively, a culturing medium or medium for product formation may be fed also to additional bioreactors.

The present invention provides a method for producing a biosynthetic product in a cascade of bioreactors comprising at least two bioreactors in flow (or fluid) communication with each other, which method comprises:

providing in the biomass production bioreactor a culturing mixture containing culturing medium and cultured microorganism;

providing in the product formation reactor (arranged after the biomass production bioreactor) a mixture containing medium for product formation, and microorganisms;

feeding at least part of the culturing mixture to the bioreactor, wherein the concentration of cells in the bioreactor is increased using a concentration device arranged before or in connection to the bioreactor.

In some embodiments the method further comprises taking part of the culturing mixture from the biomass production bioreactor, concentrating the culturing mixture taken from the biomass production bioreactor to obtain a liquid fraction and a microorganism rich fraction and feeding the microorganism rich fraction into the subsequent bioreactor.

In some embodiments the method further comprises taking part of the mixture from the bioreactor for biosynthetic product formation, concentrating the mixture taken from said bioreactor to obtain a liquid fraction and a microorganism rich fraction and feeding the microorganism rich fraction into the bioreactor or to a subsequent bioreactor in the bioreactor system.

Each bioreactor used in the present invention may be a simple container or a tank (e.g. an air lift type or stirred container or tank). The bioreactor may be used both as a growth reactor for growth of biomass as well as a product formation reactor for production of biosynthetic product. In anaerobic fermentation no aeration of the bioreactor is performed. It is preferable to be able to control one or more parameters such as temperature, pH, aeration (in case of aerobic reactor), agitation, pressure, flow rate, dilution rate, stirring, inlet, outlet redox potential, cell density and nutrient contents, as the state of the cells such as whether the cells will be growing or producing may depend on these factors. Specifically, in production of the biosynthetic product, the step of shifting from the microbial cell culture from the growth phase to the production phase occurs through inductive operation by changing one or more of the above factors or by adding an inducing factor such as a chemical. The products can be formed by primary or secondary metabolism. In a specific embodiment, the microbial growth phase and product formation phase are conducted in separate bioreactors, to allow for convenient and accurate control of culturing and product formation conditions, as well as for having a continuous production system. Further, biosynthetic products may be produced as intracellular or extracellular products, typically intracellular products are produced.

The product or products of production phase may be gaseous. The advantage of the present innovation is that by using high cell densities in production phase the product concentration in the product gas is increased.

The microorganisms are cultured and/or fermented in an array of at least two bioreactors. These at least two bioreactors are in fluid communication with each other, for example they may be connected with appropriate conduits having valves, as well as being connected through other intermediary means between the bioreactors, such as a separation stage. In one embodiment of the invention each bioreactor is in fluid connection only with the subsequent and previous bioreactor in the cascade, the bioreactor system for product formation being arranged downstream of the bioreactor system for biomass production. Having a cascade of bioreactors, between which cells may continuously be transferred, allows for continuous cell production, product formation and harvesting under optimal conditions for the cells both during growth and during product formation. In some embodiments, the bioreactors where the product formation steps are performed, are operated as any one of continuous, fed-batch or a combination of continuous and fed-batch. In one embodiment, microorganism cells are produced by fed-batch mode in one bioreactor, microorganism rich fraction is obtained and furthermore, said microorganism rich fraction is utilized for producing the biosynthetic product in another bioreactor.

In some embodiments the array of bioreactors comprises three or four or more bioreactors, which may provide certain advantages. With reference to FIG. 6 which presents an array of five bioreactors, which may be optimized for production of secondary metabolites. In FIG. 6, two biomass production reactors are used, followed by a concentration step after which cell concentrate (i.e. a microorganism rich fraction) is lead into the first of three product formation reactors. This type of setup allows the first biomass production reactor to be optimized for exponential growth, from which cells and media (i.e. a culturing mixture) is transferred into the second biomass production reactor, wherein a second type of growth media (Feed 2) is added allowing for initial nutrition depletion, and thereby inducing cells to change to product formation phase. After the second reactor, cells are concentrated in a concentration step, which produces medium permeate (microorganism poor fraction) and a cell concentrate (microorganism rich fraction). The cell concentrate is fed into the third bioreactor which is the first product formation reactor, in which a nutrient depletion media is added to the cells. The medium permeate from the cell concentration step may be recycled or discarded. From the third bioreactor the cells flow into the fourth bioreactor and from there into the fifth bioreactor after which they may be transferred into further reactors or harvested for extraction of products. In each further bioreactor, media with different nutrient content may be present, to allow for optimization of nutrient utilization and product formation. In example, cells may be carbon starved, leading to utilization of non-preferred sugars. In some embodiments, the biosynthetic product is an extracellular product, which may be extracted from the medium permeate.

Accordingly, the present method comprises one or more of the following steps:

Step A

Step a) of culturing a microorganism in the presence of culturing medium in a biomass production reactor.

The biomass production reactor may be dedicated to induction of exponential growth of the particular microorganism. When the bioreactor is operated as a growth reactor, it may be done by feeding a culturing medium comprising the optimal amount of nutrients. This may be achieved by continuously feeding to the bioreactor with new culturing medium, and continuously allowing cells to flow to the next bioreactor.

During growth, the microorganism will be using the culturing medium by metabolising the nutrients present in the medium, whereby the first bioreactor contains a microorganism culture (i.e. culturing mixture). The culturing mixture comprises the medium as well as the cultured microorganism. The advantage of this step in a continuous bioreactor set up, is that cell growth may be kept at a constant high level, and that cells may continuously be fed to the next bioreactor whether it is a further biomass production reactor or a product formation reactor. Microorganism cells may also be produced by fed-batch mode in the biomass production reactor.

Step a) may be followed by feeding the microorganism culture flow from the biomass production reactor to a concentration device (i.e. concentrating the microbial cells).

Indeed, at least part of the microorganism culture is taken from the biomass production reactor to be fed to the concentration device. Taking of microorganism culture from the biomass production reactor may in example be done in response to either high cell density or nutrient depletion in the biomass production reactor. In a continuous bioreactor system, cell density and nutrient content will be surveilled, and in order to keep such factors at a level which will keep cells growing exponentially, the speed by which culture mixture is removed from the biomass production reactor may be regulated accordingly. If cell density is too high, culture mixture may be removed and new media added.

The step of feeding the microorganism culture flow from the biomass production reactor to a concentration device thus includes taking microorganism culture (i.e. mixture of the biomass production reactor) from the biomass production reactor, and separating the cultured microorganism from the microorganism culture taken from the biomass production reactor, and thereby obtaining a microorganism rich fraction of the microorganism culture, and a microorganism poor fraction of the microorganism culture.

Steps B and C

Step b) relates to feeding, which means transferring an amount of the microorganism culture from the biomass production reactor of step a), or an amount of the microorganism rich fraction of the microorganism culture, and a medium optimized for product formation to the product formation reactor. Step c) relates to production of the biosynthetic product in the presence of the product formation medium in the product formation reactor. The microorganism cells using the medium for product formation, in the product formation phase, only grow very little, and use the nutrients in the medium for production of biosynthetic products. An advantage of feeding the microorganism rich fraction obtained from the microorganism culture of the biomass production reactor to the product formation reactor, is that certain nutrients often need to be in low amount in the medium for product formation, and by removing part of the medium in the concentration/separation step, a medium comprising low amounts of certain nutrients may be added as the medium for product formation to adjust the concentrations of e.g. nitrogen in the medium for product formation, and thereby stimulate the biosynthetic product formation.

Mixing the microorganism rich fraction with product formation media is thus done, whereby the product formation bioreactor contains a microorganism culture (i.e. mixture of the product formation bioreactor) comprising the medium optimized for product formation, together with the microorganism and the biosynthetic product which may be either intracellular or extracellular.

One embodiment of the invention comprises a step of taking part of the mixture from the product formation reactor; and separating the microorganisms from this mixture, thereby obtaining a microorganism rich fraction and a microorganism poor fraction.

One embodiment of the invention comprises a step of recycling the microorganism rich fraction to the product formation reactor. Recycling or feeding of the microorganism rich fraction to the product formation reactor may allow for further nutrient depletion of the medium for product formation, and thereby induce utilization of less preferred nutrients, e.g. sugars, resulting in a more complete use of the medium for product formation. Further, the advantage of this is that productivity of the microorganism may increase, as illustrated in the examples.

In a specific embodiment, a concentration/separation step is arranged between or in line with a growth reactor and a product formation reactor. It has been found that the productivity of the process is significantly improved if the cells obtained from a growth reactor are concentrated before feeding them to a product formation reactor or if the cells obtained from a product formation reactor are concentrated before recycling them back to said product formation reactor or feeding them to the subsequent product formation reactor thereby increasing the cell concentration in the product formation reactor. The effect is especially significant, if the biosynthetic product is produced through a secondary metabolite reaction route, in which the shift from growth to production phase has to be induced, e.g. by changing process conditions. The microorganisms may be induced to shift from growth to production phase by changing the process conditions, e.g. by changing the content of one or more nutrients in the medium for product formation by (nutrient starvation), or by other means such as by addition of an inducer, or by reduction of bioreactor volume.

The microorganism rich fraction of the microorganism culture or culturing mixture obtained from concentration steps, may have an increase in biomass concentration as compared to the biomass concentration in the bioreactor from which the mixture originated (as measured in weight %, g/l, cfu (colony forming units), or by optical density) of at least 50%, more specifically of at least 100%, such as any one of 10%, 20%, 30%, 40%, 50%, 60%, 70%, 80%, 90%, or more specifically by at least 100%.

An example of one setup of the present invention is shown in FIG. 4, where an amount of the culturing mixture of the biomass production reactor is fed to the product formation reactor (denoted product formation, nutrient depletion, concentration in FIG. 4), and where a medium for product formation may or may not be added (denoted Feed 2 in FIG. 4). Cell concentrate of the product formation reactor is recycled back to the same product formation reactor. The bioreactor set up depicted in FIG. 4 is particularly well suited for intracellular products, where the concentration step may help remove inhibitory compounds, and adjust media composition or microorganism culture and cell density in the bioreactor during the product formation phase.

Another example of the setup of the present invention is shown in FIG. 3, where an amount of the microorganism rich fraction of the biomass production reactor is fed to the product formation reactor (denoted product formation, nutrient depletion in FIG. 3), and where a medium for product formation may or may not be added (denoted Feed 2 in FIG. 4. Here, a separation/concentration step between the biomass production phase and the product formation phase or after the product formation phase allows exchange of medium or microorganism culture from the growth optimised medium or microorganism culture to a production optimised medium or microorganism culture. This may be advantageous, e.g. if the growth medium or microorganism culture comprises metabolites or nutrients which may be inhibitory for product formation, or which might influence the growth state of the cell/microorganism, and thereby inhibit the induction of product formation. Such inhibitory effects of metabolites or to nutrients are well known in the art. The method as shown in FIG. 3 is especially suitable for production of extracellular products.

In some embodiments of the invention, at least part of the microorganism culture is taken from the biomass production reactor and fed into the concentration device arranged between the biomass production reactor and the product formation reactor to obtain a microorganism rich fraction, which is fed into the product formation reactor, and at least part of the microorganism culture from the product formation reactor is taken and fed into the concentration device arranged downstream of the product formation reactor to obtain a microorganism rich fraction, which is fed into a subsequent product formation reactor (down-stream) in the cascade. One advantage may be an efficient change of culturing/medium for product formation between bioreactors, e.g. to remove inhibitory compounds and maintenance of cell density. This setup also allows for an efficient switch from growth to production phase of the cells.

In some embodiments of the present invention an amount of the microorganism rich fraction is recycled to the biomass production reactor or to the product formation reactor, such as for example between 0% and 50%, such as at least 40%, or at least 30% or at least 20% or at least 10% is recycled to the biomass production or product formation reactor, while 50% to 100%, such as all cells that are not recycled to the biomass production or product formation reactor, respectively, is carried forward to the next bioreactor.

In some embodiments, if nutrient content is not optimal, culture medium or microorganism culture of the product formation bioreactor may be removed, and new media may be added to change the content of the relevant nutrients.

In some embodiments of the present invention a third bioreactor connected serially to the product formation reactor is provided. Expanding the array with a third bioreactor allows for additional production and versatility of the methods of the present invention. A concentration step may be present between the product formation reactor and the third bioreactor, for example as illustrated in FIG. 10, but a concentration step between the product formation reactor and third bioreactor may equally also be absent. The presence of a separation step may allow increasing the microorganism/cell concentration in production reactors thus enabling a faster or more efficient utilization of carbon sources, which to improves the productivity of the production process. In processes, where the specific productivity ($g/(g*h)$) of the biosynthetic product, especially intracellular product, is low or the microorganism is slow growing, increasing the concentration of cells in the production phase enables higher productivity.

In some embodiments of the present invention, when the series of bioreactors comprises from three, four or more bioreactors, there will only be a single separation step (concentration step) between the last biomass production reactor and the first product formation reactor, or in connection to the first product formation reactor, such as exemplified in FIGS. 5, 6 and 7. In some embodiments, where an array of three, four or more bioreactors are used, an additional separation/concentration step after the third, fourth, or any subsequent bioreactors may be present, feeding the cell rich fraction back into bioreactor 3, such as is shown in FIG. 10.

In some embodiments of the present invention the method additionally comprises: i) taking part of the mixture from the product formation reactor; ii) separating the microorganism from the mixture taken from the product formation reactor, thereby obtaining a microorganism rich fraction of the mixture and a microorganism poor fraction of the mixture; iii) feeding an amount of the microorganism rich fraction of the previous step optionally together with a second medium for product formation or together with the same type of media to the third bioreactor containing the microorganism, the microorganism using the medium for product formation, whereby the third bioreactor contains a microorganism culture (i.e. mixture) of the third bioreactor, comprising the medium, the microorganism and the biosynthetic product. This separation/concentration procedure allows for a change of culturing conditions or for supplementing with certain nutrients in the late production phase, whereby cells may be switched to metabolize for example a different carbon source than that which is used in the previous bioreactor.

In some embodiments of the present invention the cascade of bioreactors additionally comprises a fourth bioreactor connected serially to the third bioreactor. One example is provided in FIG. 5, with four serially connected bioreactors, of which the first is the biomass production reactor, and the three bioreactors are product formation reactors. A separation/concentration step may be present between any of the bioreactors, as well as after the fourth bioreactor. The concentration step may be present between the product formation reactor and third bioreactor, and either recycles the cell concentrate (i.e. the microorganism rich fraction) in full or in part to the product formation reactor, or forwards the cell concentrate in full or in part to the third bioreactor. This bioreactor set up allows for a production method with four steps in which the culturing or product formation conditions may be varied in each step. This includes, for example, a biomass production step in the biomass production reactor with conditions for exponential growth, a product formation step in the product formation reactor with up-concentration of cells and nutrient depletion, a third and fourth bioreactor for product formation. In this latter process, conditions may be as shown in FIG. 9, wherein the same feed is used in bioreactors 2-4, or it may be a process in which different feeds are added to bioreactors 2, 3 and 4. The latter situation allows for change of conditions, to increase productivity, and utilization of different carbon sources.

In some embodiments of the present invention the method additionally comprises: g) taking part of the mixture from the third bioreactor; h) separating the microorganism from the mixture taken from the third bioreactor, thereby obtaining a microorganism rich fraction of the mixture and a microorganism poor fraction of the mixture; i) feeding an amount of the microorganism rich fraction, optionally together with a (third) medium for product formation to the fourth bioreactor containing the microorganism, the microorganism using the medium for product formation, whereby the fourth bioreactor contains a microorganism culture (i.e. mixture) of the fourth bioreactor comprising the medium, the microorganism and the biosynthetic product.

In some embodiments of the present invention additional bioreactors are provided, where each additional bioreactor is connected serially to the preceding bioreactor, and where the number of additional bioreactors are, 1, 2, 3, 4, 5 or 6. Cell separation or concentration steps may be present between any two bioreactors, and may feed the cell rich fraction into either the previous bioreactor or into the next bioreactor, as described herein with reference to the third and fourth bioreactors.

In some embodiments of the present invention the separation e.g. in a concentration device arranged between the biomass production reactor and the product formation reactor and/or in a concentration device arranged between the product formation reactor and the third bioreactor and/or in step h) is conducted using means selected from the list consisting of: centrifugation, filtration, settling, flocculation, flotation, decanting. In a specific embodiment, the cultured to cells are concentrated by means of any one of filtration or centrifugation or by decanting. In a specific embodiment, the cell concentration is increased in the concentration step by at least 10%, 20%, 30%, 40%, 50%, 60%, 70%, 80%, 90%, more specifically by at least 100% when compared to the concentration in the bioreactor from where it came. The inventors have found that the cells may be concentrated by at least 10% in order to have a process with improved productivity of the biosynthetic product, especially intracellular product. A microorganism rich fraction obtained from the concentration device arranged as described in this paragraph may be recycled to the same bioreactor where the microorganism culture was taken from or fed to the subsequent bioreactor.

In some embodiments of the present invention the separation is operated by state of the art, which may include continuously, semicontinuously or batch wise operated concentration devices. This may for example be achieved by using any one of the above suggested separation means, such as centrifugation, filtration, decanting, settling, flocculation or flotation. Any suitable centrifugation, filtration (e.g. depth filtration or membrane filtration such as microfiltration, ultrafiltration, nanofiltration, diafiltration, reverse osmosis including both dead-end and crossflow type arrangements), decanting, settling, flocculation or flotation methods and means are well known to a person skilled in the art and may be utilized in the present invention.

The entire bioreactor system may also be operated in a continuous manner, and in addition to the continuous operation of the separation step(s) all the bioreactors are also run in a continuous mode. In addition to means for running the separation step(s) in a continuous manner, means allowing for a continuous flow of cells between bioreactors have to be employed as well. Alternatively, the method of the present invention may be operated in a fed-batch manner, wherein the concentration may be operated in a batch or continuous manner depending on the concentration technique used.

In some embodiments of the present invention an amount of the microorganism culture in each of the serially connected bioreactors is fed into the subsequent bioreactor of the array of serially connected bioreactors. This procedure allows for a flow of microorganisms all the way through the bioreactor system, to expose the microorganism to all the different conditions in the different bioreactors, whereby the organism is led to produce the biosynthetic product, especially intracellular product, efficiently. It also allows for an amount of fresh microorganism obtained in the culturing step to be successively carried through all the bioreactors.

In some embodiments of the present invention particular reaction conditions are provided to the bioreactors. For example, independently of each other the biomass production bioreactor, the product formation reactor, as well as the third and fourth bioreactors (if present) may be optimised according to the following. A bioreactor preceding the biomass production reactor, and serially connected to or in flow connection with the biomass production reactor, may additionally be present, and may be optimised for microorganism growth. The biomass production reactor may be optimised for microorganism growth at late stage exponential phase and/or optimised for induction of biosynthetic product formation e.g. by nutritional starvation. The product formation reactor may be optimised for biosynthetic product formation at a stationary growth phase, optionally under nutrient starvation conditions. The third bioreactor may be optimised for biosynthetic product formation with minimal carbon source addition.

In some embodiments the method comprise the following steps: j) bioreactor preceding the biomass production reactor and serially connected to or in flow connection with the biomass production reactor, where the bioreactor preceding the biomass production reactor is optimised for microorganism growth; k) The biomass production reactor optimised for microorganism growth at late stage exponential phase and/or optimised for induction of nutritional starvation; l) the product formation reactor optimised for biosynthetic product formation at a stationary growth phase, optionally under nutrient starvation conditions; m) the third bioreactor optimised for biosynthetic product formation with minimal carbon source addition, which results in residual sugar consumption. This procedure may in one embodiment be in a fed batch culture, where cell separation steps ensure that media, microorganism culture and culture conditions may be changed between each step. The procedure is performed in a cascade bioreactor system, such as a fed-batch or continuous culture bioreactor setup, where steps j) to m) are performed in a cascade.

In some embodiments only two or three of the: preceding (j), biomass production (k), product formation (l) and third (m) bioreactors are present.

In some embodiments, the method comprises the following steps: j), k), l), and m), with a cell separation step between steps k) and l) wherein the cell rich fraction is fed into l), for example as illustrated in the array shown in FIG. 7.

In some embodiments, the method comprises the following steps: j), l) and m), with cell separation steps positioned after each of l) and m), and wherein the cell rich fraction is fed back into each of l) and m), for example as illustrated in the array shown in FIG. 10.

In some embodiments of the present invention the cell mass concentration is increased by one or more method steps or one or more concentration devices, wherein the microorganism rich fraction is obtained at a temperature between 3 to 80° C. (e.g. 3 to 30° C. or 31 to 80° C.) lower than the bioreactor from which the microorganism culture was taken from and/or wherein the temperature of the microorganism culture to be fed into the concentration device is lowered by 3 to 80° C. (e.g. 3 to 30° C. or 31 to 80° C.).

In some embodiments of the present invention the one or more separations into a microorganism rich fraction and a microorganism poor fraction is conducted at a temperature in the range between 1 to 30° C. lower (e.g. 3 to 30° C. lower) than the bioreactor from which the mixture to be separated was taken from and/or where the temperature of the mixture to be separated is lowered by 1 to 30° C. (e.g. lowered by 3 to 30° C.). In a specific embodiment, the temperature of the microorganism culture obtained from a bioreactor is lowered before and/or during a concentration step. Without wanting to be bound by any particular theory, the inventors believe that the concentration step may cause stress to cells thereby reducing productivity in the later steps and that a temperature decrease of the microorganism/cells alleviate the stress to a certain extent compared to no temperature decrease. This maintains the activity of the cells, which improves production efficiency of cells in the bioreactors.

In one specific embodiment, the temperature of the microorganism culture is lowered by at least 1° C., such as between 1 and 5° C., or 1 and 10° C., or 1 and 15° C. or 1 and 20° C. or between 1 and 30° C., such as between 5 and 15° C., or between 15 and 25° C. before or during the concentration step.

In another specific embodiment, the temperature is lowered by at least 1%, such as any one of at least 2%, 3%, 4%, 5%, 10%, 15%, 20%, 25%, 30%, 40%, 50%, 60%, 70%, 80%, or at least 90% of the temperature in the bioreactor from which the cells were derived, as measured in ° C. In a specific embodiment, the temperature is normalized after the concentration step, i.e. returned to the original temperature or changed to a specific temperature optimized for production formation, wherein the temperature is typically between 20° C. and 80° C., specifically between 25° C. and 37° C. Some advantages associated with a temperature reduction step may be considerably lower cell loss during the concentration step. Furthermore, the temperature reduction step may in addition shift the microorganism/cells into a more stationary phase, thereby promoting biosynthetic product formation.

Furthermore, in some embodiments of the invention in case the microorganism is a transgenic organism and the product being a product of the transgene which is controlled by a heat sensitive promoter, such as a heat shock promoter, a temperature shift (i.e. increase of temperature) may be used to induce expression of the product. In such cases, a temperature changes during and/or after the concentration step may be used to induce expression of the product. Different heat shock promoters may require different temperature shift levels to be activated. In example, in Zebrafish, a 9.5° C. from 28.5° C. to 38° C. raise in temperature induce gene expression greatly in heat shock regulated genes. In *Drosophila* cells, the optimal temperature shift is from e.g. 25° C. to between 36 and 37° C., whereas in *Saccharomyces cerevisiae* the optimal temperature shift is from e.g. 25° C. to between 39 and 40° C. So in some embodiments, the microorganism used in the present invention is a transgenic or transfected microorganism wherein the transgene or transfected DNA comprises a gene of interest for production of a biosynthetic product, and wherein the expression of the gene of interest is controlled by a heat shock promoter. In such embodiments where the gene of interest is controlled by a heat shock promoter, the temperature before or during the production phase may be raised by at least 2° C., such as at least 3° C., or at least 4° C., such as at least 5° C., such as between 2 and 15° C., or between 5 and 15° C., such as any one of 5° C., 6° C., 7° C., 8° C., 9° C., 10° C., 11° C., 12° C., 13° C., 14° C. or 15° C. The temperature increase may be temporary to induce expression, or may be permanent during the production phase.

In some embodiments, expression of an introduced gene of interest is controlled by a carbon source dependent promoter, such as in *Saccaromyces cerevisiae*, where certain promoters may be induced by lack of glucose (Weinhandl et al. Microbial Cell Factories, 2014, 13:5). Other useful promoters which may be induced by a variety of factors are well known in the art, in non-limiting example, such a promoter may be the yeast Tet-Promoters which are inducible by addition of tetracycline may be used. Copper ion inducible promoter systems are also known in the art, and may be used for regulating expression of genes of interest in the present invention. In some embodiments constitutively active promoters may be used to express a gene of interest for production of a biosynthetic product.

The biosynthetic product produced by the present invention is typically an intracellular product, but it may be one or more of the following: i) biomass from the cultured microorganism; ii) a primary metabolite; iii) a secondary metabolite; iv) an extracellular product. The biosynthetic product may be selected from one or more classes of compounds selected from the list of: alcohols, acids, enzymes, lipids, antibiotics, proteins, polymers or mixtures thereof. The product may be the result of genetic engineering of a cell, method of making such are well known in the art. In genetically engineered cells, production of the product is induced by presence of a certain factor in the media, or by temperature shift, or the product may be constitutively expressed without induction. Further, the product may be one, the production of which is triggered by certain conditions, such as presence or lack of specific nutrients, temperature, pH or other. As described above, the biosynthetic product may be one or more organic compounds produced by a microorganism. In a specific embodiment, the biosynthetic product comprises any one of lipids, alcohols, enzymes, antibiotics, proteins, polymers, acids, diacids or any mixture of these.

Specific process conditions such as temperature, nutrient levels, pH may be provided for microorganisms to produce the wide variety of different organic compounds. These compounds may be considered intracellular products or extracellular products. Examples of intracellular products may be microbial enzymes such as: catalase and many others. Recombinant proteins, such as hepatitis B vaccine, interferon, granulocyte colony-stimulating factor, streptokinase and others are also intracellular products. However, most enzymes are produced as extracellular products.

A specific intracellular product by primary metabolism may for example be single cell protein, which may be produced by many different microorganisms, such as algae, yeasts, fungi or bacteria. Example of a potential use for this may include protein additive to feeds for both human and animal use. The production of intracellular products which are secondary metabolites are also preferred, and may in non-limiting example encompass microbial oil (e.g. produced under N, P, S, Fe etc. starvation conditions), wax esters (e.g. produced under N starvation conditions) and polyhydroxyalkanoate (PHA) (e.g. produced under N, P, S, Fe etc. starvation conditions), which may be by either aerobic or anaerobic conditions. Different microorganisms are well known for their ability to produce either short chain length PHA, or medium chain length PHA). Ergotamine, produced by *Claviceps purpurea* organisms are also secondary metabolites of interest as products of the disclosed processes.

Extracellular products include primary metabolites and secondary metabolites. Primary metabolites may be produced by aerobic or anaerobic production. In some instances, a change from anaerobic to aerobic or from aerobic to anaerobic/microaerobic conditions are needed during production processes.

Extracellular biosynthetic products include but are not limited to for example insulin, amylase, protease, pectinase, glucose isomerase, cellulase, hemicellulase, lipase, lactase, streptokinase, microbial oil (e.g. produced under N, P, S, Fe etc. starvation conditions), isoprenoids (e.g. produced under N starvation conditions), ethanol, acetic acid, butyric acid, succinic acid, lactic acid, propionic acid, malic acid, fumaric acid, pyruvic acid, n-Butanol, iso-butanol, 1,3-propanediol, 1,4-butanediol, ABE or IBE-fermentation, which is a two-stage process and which is preferred, citric acid (e.g. under Fe-starvation conditions), amino acids, glutamic acid (e.g. under nutrient deprivation and low biotin conditions), vinegar (acetic acid produced from ethanol), 3-hydroxypropionic acid (HPA), 3-hydroxybutyric acid, 2,3-butanediol, isopropanol, L-isopropanol, itaconic acid (e.g. under P-starvation conditions), gluconic acid, adipic acid, microbial lipid, litaconic acid, enzymes, antibiotics, fatty acid derivatives, terpenoids, hydrocarbons, hydroxyalkanoic acids (and derivatives thereof), isobutene, and vitamins such as riboflavin.

The carbon sources may be sugars during the growth phase and oils during the product formation phases. The carbon source may be selected from the group consisting of sugars (e.g. molasses or lignocellulose derived sugars), fats or oils or lipids (e.g. waxes, wax esters, sterols, terpenoids, isoprenoids, carotenoids, polyhydroxyalkanoates, nucleic acids, fatty acids, fatty acid derivates, fatty alcohols, fatty aldehydes, fatty acid esters, fatty amines, medium and long chain dicarboxylic acids, epoxy fatty acids, long chain diols and polyols, phospholipids, glycolipids, sphingolipids or acylglycerols, such as triacylglycerols, diacylglycerols, or monoacylglycerols), gases (e.g. synthesis gas) and any combinations thereof. However, the carbon sources suitable for the present invention are not limited to above group. In different method steps of the present invention the carbon source may be selected independently from other carbon sources used in other method steps.

In one embodiment a carbon source or carbon sources are gaseous. The advantage of the present innovation is that by having high cell densities in the product formation phase the uptake rate of carbon source from gas phase is improved and thus the residual carbon source concentration in the fermentation off gas is lower. This also improves the overall yield of product versus fed carbon source.

Formation of biosynthetic products by secondary metabolism may be accomplished by the methods of the present invention. Such products are typically formed during the late exponential or stationary growth phase, and may for example be selected from the list of enzymes (induction needed), antibiotics, fatty acid derivatives, isoprenoids, terpenoids etc. hydrocarbons, hydroxyalkanoic acids (and derivatives thereof, isobutene, gaseous products), and vitamins such as riboflavin.

In some embodiments of the present invention the biosynthetic product is one or more lipids selected from the list consisting of: long chain diacids, hydroxyl fatty acids, long chain diols, fats, oils, waxes, farnesene type products, wax esters, sterols, terpenoids, isoprenoids, carotenoids, polyhydroxyalkanoates, nucleic acids, fatty acids, fatty acid derivates, fatty alcohols, fatty aldehydes, fatty acid esters, fatty amines, medium and long chain dicarboxylic acids, epoxy fatty acids, long chain diols and polyols, phospholipids, glycolipids, sphingolipids and acylglycerols, such as triacylglycerols, diacylglycerols, or monoacylglycerols. Microorganisms capable of producing such compounds are well known in the art. The present invention provides cost effective bioreactor setup allowing for use of convenient methods for efficient production of these types of compounds.

The present invention also provides a cascade of serially connected bioreactors or a bioreactor system comprising at least two serially connected bioreactors and one or more cell concentration devices positioned between and in line with or in connection to two serially connected bioreactors in said array of bioreactors. Such bioreactors will in a specific embodiment for aerobic production of biosynthetic products, have means for stirring and aeration, or may be air lift bioreactors. In some specific embodiments where fermentation is anaerobic, stirred bioreactors or bioreactors which do not use air lift for agitation of cells may be utilized. In some other specific embodiments where fermentation is anaerobic and the carbon source(s) is (are) gaseous, air lift type bioreactors (e.g. bubble column) may be utilized.

In some embodiments of the present invention the one or more cell concentration devices are positioned between and in line with each two serially connected bioreactors in said array of bioreactors.

In some embodiments of the present invention an array of at least three serially connected bioreactors is provided.

Such a bioreactor setup allows for exposing the cells to at least three different culturing conditions, and allows the bioreactors to be run in a continuous manner, or in a fed batch mode. This means that the cells may for example be subjected to conditions for exponential growth, late exponential growth and production in individual bioreactors.

In some embodiments of the present invention an array of at least four serially connected bioreactors is provided. Such a bioreactor setup allows for exposing the cells to at least four different culturing conditions if the bioreactors are run in a continuous manner. This means that the cells may be subjected to conditions for exponential growth, late exponential growth production and production.

In some embodiments, the invention presents a process for production of biosynthetic products wherein the process comprises the steps presented in FIG. 1 (Embodiment A) and FIG. 2 (Embodiment B):

Embodiment A: A process for production of microbial products or biosynthetic products, comprising a cascade of steps serially connected to each other, wherein the first step comprises k number of parallel biomass production reactors, followed by m number of parallel first product formation reactors, followed by n number of parallel second product formation reactors, and wherein the first product formation reactors are connected to or in flow connection with one or more concentration devices positioned to extract microorganism rich fraction and microorganism poor fraction from the first production reactors and recycle the microorganism rich fraction back to the first product formation reactors.

Embodiment A.1: a process according to embodiment A, wherein K=1-x, such as anyone from 1 to 50, such as anyone from 1 to 25, such as anyone from 1 to 10, such as any one of 1, 2, 3, 4, 5, 6, 7, 8, 9 or 10.

Embodiment A.2: a process according to embodiment A or A.1, wherein m=1-y, such as anyone from 1 to 50, such as anyone from 1 to 25, such as anyone from 1 to 10, such as any one of 1, 2, 3, 4, 5, 6, 7, 8, 9 or 10.

Embodiment A.3: a process according to embodiment A, A.1 or A.2, wherein n=0-z, such as anyone from 0 to 50, such as anyone from 1 to 25, such as anyone from 1 to 10, such as any one of 0, 1, 2, 3, 4, 5, 6, 7, 8, 9 or 10.

Embodiment A.4: a process according to any one of embodiments A, A.1, A.2, or A.3, wherein the individual feeds to the bioreactors k, m and n are of the same composition.

Embodiment A.5: a process according to any one of embodiments A, A.1, A.2, or A.3, wherein the individual feeds to the bioreactors k, m and n are of different composition.

Embodiment B: A process for production of microbial products or biosynthetic products, comprising a cascade of steps, wherein the first step comprises k number of parallel biomass production reactors, followed by m number of first product formation reactors, followed by n number of second product formation reactors, and wherein one or more concentration devices are positioned between the biomass production reactors and the first product formation reactors to extract microorganism rich fraction and microorganism poor fraction from the biomass production reactors and pass the microorganism rich fraction forward into the first product formation reactors.

Embodiment B.1: a process according to embodiment B, wherein K=1-x, such as anyone from 1 to 50, such as anyone from 1 to 25, such as anyone from 1 to 10, such as any one of 1, 2, 3, 4, 5, 6, 7, 8, 9 or 10.

Embodiment B.2: a process according to embodiment B or B.1, wherein m=1-y, such as anyone from 1 to 50, such as anyone from 1 to 25, such as anyone from 1 to 10, such as any one of 1, 2, 3, 4, 5, 6, 7, 8, 9 or 10.

Embodiment B.3: a process according to embodiment B, B.1 or B.2, wherein n=0-z, such as anyone from 0 to 50, such as anyone from 0 to 25, such as anyone from 0 to 10, such as any one of 0, 1, 2, 3, 4, 5, 6, 7, 8, 9 or 10.

Embodiment B.4: a process according to any one of embodiments B, B.1, B.2, or B.3, wherein the individual feeds to the bioreactors k, m and n are of the same composition.

Embodiment B.5: a process according to any one of embodiments B, B.1, B.2, or B.3, wherein the individual feeds to the bioreactors k, m and n are of different composition.

In some embodiments according to any one of embodiments A-B5, a first growth step is optimized for exponential growth, and the second growth step is for late stage exponential growth.

In some embodiments according to any one of embodiments A-B5, a first product formation step is for production of biosynthetic product, and the second product formation step is for production of biosynthetic product under nutrient starvation.

In some embodiments according to any one of embodiments A-B5, microbial cell status regarding growth is controlled by one or more of nutrients, pH, temperature, cell density, amount of inhibitory metabolic waste products, carbon source accessibility, oxygen content in media (in case of aerobic reactor), agitation, pressure, flow rate, dilution rate, stirring, inlet, outlet and redox potential.

In some embodiments according to any one of embodiments A-B5, microbial cell status regarding production of biosynthetic products is controlled by one or more of nutrients, pH, temperature, cell density, amount of inhibitory metabolic waste products, carbon source accessibility, oxygen content in media (in case of aerobic reactor), production inducing factors, agitation, pressure, flow rate, dilution rate, stirring, inlet, outlet and redox potential.

In some embodiments, the present invention is used for microbial oil production. This has been exemplified in the following:

The cultivation is performed in any kind of bioreactor that is supplied with air, such as stirred tank bioreactors or air lift bioreactors. Bioreactor types can be optimized based on the process requirements and different bioreactor types can be used in one cascade. Typically the biomass production phase (first bioreactor in a cascade or the biomass production reactor) requires the highest oxygen transfer rate while oil production phase does not require as high oxygen transfer rate. According to one embodiment of the invention air-lift bioreactors are used in the cascade. According to another embodiment of the invention both stirred tank bioreactors and air-lift bioreactors may be used in the cascade.

In a specific embodiment the bioreactor system comprises at least two bioreactors which are used in a cascade and a cell concentration step arranged between the biomass growth and oil production phases for microbial oil production, (see FIG. 3). The concentration step may alternatively be positioned after the production reactor, in which case the cell concentrate is fed back into the production reactor (FIG. 4). In a specific embodiment, the bioreactor system comprises at least three bioreactors, even more specifically at least four bioreactors, which are used in a cascade with the following set-up and which are operated in continuous mode (FIG. 5). The operation of different bioreactors in the cascade in an exemplified cultivation process for microbial oil production comprising four bioreactors is additionally described below:

Bioreactor 1 (first bioreactor in a cascade) is used to cultivate microorganism biomass and is fed with cultivation medium containing adequate amounts of nutrients allowing efficient biomass growth. Thus, bioreactor 1 is operated at the maximum growth phase of the growth curve. The cell concentration in bioreactor one is at least 10 g/l, more specifically at least 20 g/l, even more specifically at least 40 g/l. The lipid content of microbial biomass in bioreactor 1 is typically less than 20% of cell dry weight. Depending on which microorganism is to used, different nutrient content may be present in the media, e.g. typically the carbon to nitrogen ratio will be less than 100.

Cell concentration, such as centrifugation decanting or filtration, is performed after the first bioreactor resulting in an increase in biomass concentration as compared to the biomass concentration in the bioreactor from which the mixture originated (weight % as measured in g/l, cfu (colony forming units), or by optical density) of at least 50%, more specifically of at least 100%, such as any one of 10%, 20%, 30%, 40%, 50%, 60%, 70%, 80%, 90%, or more specifically by at least 100%.

The purpose of bioreactor 2 (second bioreactor) is to induce nutrient starvation and lipid production of microorganisms. Thus, the bioreactor is operated at the late exponential phase in the growth curve. Specifically, bioreactor 2 is operated so that nitrogen (or other nutrient such as. P, Fe or S) is consumed by microorganisms. The biomass concentration in bioreactor 2 is specifically at least 30 g/L, more specifically at least 60 g/l, more specifically at least 80 g/l. The lipid content of microbial biomass in bioreactor 2 is typically less than 20% of cell dry weight.

The purpose of bioreactor 3 (third bioreactor) is to produce oil which is produced in the secondary metabolism. The bioreactor is operated in the stationary growth phase of the growth curve. Specifically, bioreactor 3 is operated in the nitrogen (or other nutrient such as. P, Fe or S) starvation to achieve efficient lipid production. The biomass concentration in bioreactor 3 is specifically at least 50 g/l, more specifically at least 80 g/l, more specifically at least 120 g/l. The lipid content of microbial biomass in bioreactor 3 is typically more than 30% of cell dry weight, more specifically at least 40% of cell dry weight.

The purpose of bioreactor 4 (fourth bioreactor) is to produce oil and to consume residual sugars from the growth medium. The bioreactor is operated in the (late) stationary growth phase of the growth curve. Specifically, bioreactor 4 is operated in the nitrogen (or other nutrient such as. P, Fe or S) starvation and addition of carbon source is minimal, i.e. bioreactor 4 is run at near carbon limitation. Especially when the growth medium includes mixed sugars, the carbon components, which are more difficult to use by the microorganisms, are used in the last bioreactor.

Bioreactor 4 is used to minimize sugar loss by allowing microorganisms to utilize residual sugars including sugars that are not preferred by microorganisms. The biomass concentration in bioreactor 3 is specifically at least 60 g/l, more specifically at least 100 g/l, more specifically at least 150 g/l. The lipid content of microbial biomass in bioreactor 4 is typically more than 30% of cell dry weight, more specifically at least 40% of cell dry weight, even more specifically at least 50%, even more specifically at least 60%.

After bioreactor 4, microorganism cells are collected from microorganism culture and the biosynthetic product (e.g. microbial lipid) is recovered. Where the biosynthetic product is microbial lipid, the overall lipid productivity calculated over the cultivation (over the whole process) according to the invention is at least 0.3 g/(l*h), specifically at least 0.5 g/(l*h), more specifically at least 1.0 g/(l*h), more specifically at least 1.5 g/(l*h), more specifically at least 2.0 g/(l*h), even more specifically at least 2.5 g/(l*h).

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The terms "comprising", "comprise" and comprises herein are intended by the inventors to be optionally substitutable with the terms "consisting of", "consist of" and "consists of", respectively, in every instance.

EXAMPLES

Example 1—*Rhodosporidium fluviale*, Lipid Production in Fed-Batch Cultivation

*Rhodosporidium fluviale* strain CBS 9465 was cultivated in 10 l scale bioreactor in glucose fed-batch cultivation for microbial oil production.

For inoculum production following preculture medium was prepared consisting of (per liter of water):glucose 40 g; yeast extract 5 g; $(NH_4)_2SO_4$ 2.5 g; $K_2HPO_4$ 0.5 g; $KH_2PO_4$ 1.0 g; $MgSO_4 \times 7H_2O$ 1.0 g; $CaCl_2 \cdot 2H_2O$ 0.1 g. Medium was divided in 50 ml batches and was sterilized by autoclaving at 121° C. for 15 min. Preculture medium was inoculated with 1% inoculum and incubated at 30° C. temperature for 18 hours.

Culture medium composed of per liter of water:glucose 40 g; yeast extract 8 g; $(NH_4)_2SO_4$ 3.5 g; $KH_2PO_4$ 7 g; $MgSO_4 \cdot 7H_2O$ 2.5 g; $CaCl_2 \cdot 2H_2O$ 0.1 g; $ZnSO_4 \cdot 7H_2O$ 0.0008 g; $CuCl_2 \cdot 2H_2O$ 0.00008 g; $MnSO_4 \cdot H_2O$ 0.0008 g; $FeSO_4$ 0.0004 g and $NaHPO_4$ 0.5 g. Medium was in situ sterilized at 121° C. for 15 min.

Culture medium was inoculated with 10% inoculum and after inoculation the starting volume was 8 l. The cultivation was done at 30° C. temperature. During cultivation pH was maintained at 6 by adjusting with 3 M NaOH. Aeration rate was 1 vvm and $pO_2$ (dissolved oxygen) was maintained above 20% using agitation cascade with max 1000 rpm agitation rate. Struktol J647 was used as antifoam agent and it was pulsed to the cultivation periodically throughout the cultivation. After 23 h cultivation additional 4 g/l yeast extract was added to the culture medium. During cultivation 54% glucose solution fed to the culture to maintain glucose concentration at 5-60 g/l. Total cultivation time was 95 h.

During the 95 h cultivation in total 85 g/l biomass with 61% lipid content (per dry weight) were formed, the overall volumetric lipid productivity being 0.54 g/(lh) at the end of cultivation. Maximum volumetric lipid productivity of 0.56 g/(lh) was achieved after 76.5 h incubation with 75 g/l cell dry weight content containing 58% lipids.

Example 2—*Rhodosporidium Fluviale*, Lipid Production in Two Step Fed-Batch Cultivation with Interim Concentration

*Rhodosporidium fluviale* strain CBS 9465 was cultivated in two step glucose fed-batch cultivation with interim concentration for microbial oil production.

For inoculum production culture medium was prepared consisting of (per liter of water):glucose 40 g; yeast extract 5 g; $(NH_4)_2SO_4$ 2.5 g; $K_2HPO_4$ 0.5 g; $KH_2PO_4$ 1.0 g; $MgSO_4·7H_2O$ 1.0 g; $CaCl_2·2H_2O$ 0.1 g. Medium was divided in 50 ml batches and was sterilized by autoclaving at 121° C. for 15 min. Preculture medium was inoculated with 1% inoculum and incubated at 30° C. temperature for 18 hours.

Culture medium for biomass production step consisted of (per liter of tap water):glucose 40 g; yeast extract 8 g; $(NH_4)_2SO_4$ 2.5 g; $MgSO_4·7H_2O$ 1.5 g; $KH_2PO_4$ 5.0 g; $CaCl_2·2H_2O$ 0.1 g. Medium was in situ sterilized at 121° C. for 15 min. After sterilization chloramphenicol suspended in ethanol was added to the medium give chloramphenicol concentration of 0.1 g/l.

Biomass production was done in two parallel bioreactors to obtain enough bioreactor volume. bioreactors were inoculated with 10% inoculum and after inoculation the starting volume was 10 l in both bioreactors, thus the overall volume for biomass production was 20 l. Cultivation parameters for biomass production and concentration steps were: temperature 30° C., pH was maintained at 6 by adjusting with 3 M NaOH, aeration rate was 1 vvm and the $pO_2$ (dissolved oxygen) was maintained above 30% using stirring cascade with max 1000 rpm agitation rate. Cultivations were fed with 54% glucose solution to maintain glucose concentration between 5-60 g/l.

After 18 h cultivation cell concentration step was started. Cells were concentrated by using a cross flow filter (Pellicon 2 Mini with two Durapore 0.45 µm cassettes) connected to the bioreactors. During concentration the parallel cultures were combined in to one bioreactor. Concentration time was 6 h and the total culture volume after concentration was 7 l.

After the concentration step following supplementing nutrient solutions were added to the bioreactor: 7 g $MgSO_4·7H_2O$ in 20 ml water; 21 g $KH_2PO_4$ in 20 ml water and 34 g Yeast Nitrogen Base without Ammonium Sulphate and Amino Acids in 600 ml water.

Cultivation parameters after concentration step were: temperature 30° C., pH was maintained at 6 by adjusting with 3 M NaOH, aeration rate was 1 vvm and the $pO_2$ was maintained above 20% using stirring cascade with max 1000 rpm agitation rate. Cultivation was fed with 54% glucose solution or dry glucose to maintain glucose concentration between 5-60 g/l. This lipid production phase was continued for 67 h. Culture volume at the end of cultivation was 9.5 l.

After 18 h biomass production step the biomass concentration was 29 g/l. During concentration step biomass was concentrated to 95 g/l concentration. After the concentration biomass and lipid production were continued and the final biomass concentration was 148 g/l, of which 42% was lipids. The overall lipid productivity was 0.60 g/(l*h). Compared to batch cultivation 7% improvement in volumetric lipid productivity was achieved.

Example 3—*Rhodosporidium fluviale*, Lipid Production in Two Step Fed-Batch Cultivation with Interim Concentration

*Rhodosporidium fluviale* strain CBS 9465 was cultivated in two step glucose fed-batch cultivation with interim concentration for microbial oil production.

For inoculum production culture medium was prepared consisting of (per liter of water):glucose 40 g; yeast extract 5 g; $(NH_4)_2SO_4$ 2.5 g; $K_2HPO_4$ 0.5 g; $KH_2PO_4$ 1.0 g; $MgSO_4×7H_2O$ 1.0 g; $CaCl_2·2H_2O$ 0.1 g. Medium divided in 100 ml batches was sterilized by autoclaving at 121° C. for 15 min. Preculture media were inoculated with 1% inoculum and incubated at 29° C. temperature for 18 hours.

Culture medium for biomass production step consisted of (per liter of tap water):glucose 40 g; yeast extract 8 g; $(NH_4)_2SO_4$ 2.5 g; $MgSO_4·7H_2O$ 1.5 g; $KH_2PO_4$ 5.0 g; $CaCl_2·2H_2O$ 0.1 g. Medium was in situ sterilized at 121° C. for 15 min. After sterilization chloramphenicol suspended in ethanol was added to the medium give chloramphenicol concentration of 0.1 g/l.

Biomass production was done simultaneously in three parallel bioreactors with working volumes 4, 10 and 10 L after inoculation with 15% inoculum. The overall volume for biomass production was thus 24l. Cultivation parameters for biomass production were: temperature 29° C., pH was maintained at 6 by adjusting with 3 M NaOH, aeration rate was 1 vvm and the $pO_2$ was maintained above 30% using stirring cascade with max 1000 rpm agitation rate. Cultivations were fed with 54% glucose solution to maintain glucose concentration between 5-60 g/l.

After 26 h cultivation cell concentration step was started. Cells were concentrated by using a cross flow filter (Pellicon 2 Mini with three Durapore 0.45 µm cassettes) connected to the bioreactors. During concentration step cultivation temperature was maintained at 20° C. Concentration time was 6 h and the total culture volume combined to one 10 L bioreactor was 6 L after the concentration step.

After the concentration step following supplementing nutrient solutions were added to the bioreactor: 7 g $MgSO_4·7H_2O$ in 20 ml water; 21 g $KH_2PO_4$ in 20 ml water and 34 g Yeast Nitrogen Base without Ammonium Sulphate and Amino Acids in 600 ml water.

Cultivation parameters after concentration step were: temperature 29° C., pH was maintained at 6 by adjusting with 3 M NaOH, aeration rate was 1 vvm and the $pO_2$ was maintained above 20% using stirring cascade with max 1000 rpm agitation rate. Cultivation was fed with 54% glucose solution or dry glucose to maintain glucose concentration between 5-60 g/l. This lipid production phase was continued for 67.5 h. Culture volume at the end of cultivation was 8.8 l.

After 18 h biomass production step the biomass concentration was 29 g/l. During concentration step biomass was concentrated to 137 g/l concentration. After the concentration biomass and lipid production were continued and the final biomass concentration was 189 g/l, of which 69% was lipids.

The maximum productivity was 0.90 g/(l*h) after 78 h cultivation. By this method 38% increase in volumetric lipid productivity was achieved compared to batch cultivation.

Example 4—*Rhodosporidium fluviale*, Lipid Production in Two Step Continuous Cultivation

*Rhodosporidium fluviale* strain CBS 9465 was cultivated in two step continuous cultivation for microbial oil production.

Generalized view of the equipment used in the cultivation is shown in FIG. 5. Culture media were prepared as batches in medium sterilization tank and transferred to media tanks for storage. Microbial cell culturing was started with a batch phase in biomass production bioreactor to allow cells to propagate before the start of continuous operation. Similar biomass propagation was not performed in oil production bioreactor.

After suitable propagation time continuous culturing for biosynthetic product formation was started. Biomass production bioreactor was continuously fed with media from media storage tanks. Biomass production bioreactor was operated in overflow mode and culture was continuous transferred forward via dip tube.

As the bioreactors used for the demonstration were very different in size, in order to achieve intended dilution rates in oil production bioreactor, only portion of the culture from biomass production was directed to oil production. Rest of the culture from biomass production bioreactor was directed to biomass waste collection tank. In addition to culture continuously transferred from biomass production bioreactor 50% glucose solution was also added continuously to oil production bioreactor. Similarly to biomass production, oil production was operated in overflow mode and culture was continuously transferred to collection tank via dip tube.

For inoculum production culture medium was prepared consisting of (per liter of water): 40 g glucose, 5 g yeast extract, 2.5 g $(NH_4)_2SO_4$, 0.83 g $MgCl_2 \times 6H_2O$, 0.53 g $K_2HPO_4$, 1 g $KH_2PO_4$ and 0.2 g $CaCl_2 \times 2H_2O$. Media components were dissolved in tap water. Medium divided in 50 ml batches was sterilized by autoclaving at 121° C. for 20 min. Preculture media were inoculated with 1% inoculum of *Rhodosporidium fluviale* CBS 9465 yeast and incubated at 30° C. temperature for 27 hours in orbital shaker using 250 rpm agitation rate.

Culture medium for batch biomass propagation consisted of (per liter of water): 5 g yeast extract, 2 g $(NH_4)_2SO_4$, 2 g $MgCl_2 \times 6H_2O$, 7 g $KH_2PO_4$, 0.4 g $CaCl_2 \times 2H_2O$, 0.03 g $MnSO_4 \times H_2O$, 0.0003 g $ZnSO_4 \times 7H_2O$, 0.0002 g $CuCl \times 2H_2O$, 0.0002 g $Na_2MoO_4 \cdot 2H_2O$ and 0.2 g Struktol J647. Medium volume was 60 l. Components were dissolved in tap water and the medium was in situ sterilized at 121° C. for 30 min. After sterilization 6 kg of sterile 50% glucose syrup was added aseptically to the medium. Oil production bioreactors were filled with water and sterilized.

Biomass propagation medium was inoculated with 1.7% preculture. Cultivation parameters for biomass propagation were: temperature 30° C., pH was maintained at 5.5 by adjusting with 3 M $NH_4OH$, aeration rate was 1.2 vvm and agitation rate was 200 rpm.

After 21 h cell propagation in biomass production bioreactor, continuous two step culturing was initiated by starting the medium feed from medium storage tanks to biomass production bioreactor, culture transfers from biomass production to oil production bioreactor and to collection tank, biomass transfer from oil production bioreactors to collection tank and glucose feed to oil production bioreactor.

Culture media fed to biomass production bioreactor during continuous operation consisted of (per liter of water): 54.5 g glucose, 8 g yeast extract, 7 g $KH_2PO_4$, 1.5 (or 1.8) g $MgCl_2 \times 6H_2O$ (or $MgSO_4 \times 7H_2O$), 0.5 g $(NH_4)_2SO_4$, 0.03 g $MnSO_4 \times H_2O$ (or $MnCl_2 \times 4H_2O$), 0.0005 g $ZnSO_4 \times 7H_2O$, 0.0002 g $CuCl \times 2H_2O$, 0.0002 g $Na_2MoO_4 \cdot 2H_2O$, 0.002 g $FeSO_4 \cdot 7H_2O$, 0.1 g chloramphenicol, 0.0125.10-3 g biotin, 0.00125 g thiamin HCl, 0.00025 g vitamin B12, 0.00125 g pantothenic acid and 0.06-0.18 g Struktol J647. With the exception of ammonium and magnesium salts, all minerals, glucose, yeast extract and struktol were dissolved in tap water and the medium base was in situ sterilized in the medium sterilization tank at 121° C. for 30 min forming the medium base. Separate stock solutions were prepared of ammonium and magnesium salts. Solutions were sterilized by autoclaving at 121° C. for 20 min and added aseptically to the sterilized medium base. Vitamins were dissolved in MQ water, sterile filtered and added aseptically to the sterilized medium base. Chloramphenicol was dissolved in ethanol and added aseptically to the sterilized medium base.

Cultivation parameters for biomass production during continuous operation were: flow rate to biomass production bioreactor 11 l/h (dilution rate 0.21 $h^{-1}$), temperature 29-30° C., pH was adjusted to 5.0 with 3 M $NH_4OH$ and foaming was controlled by automatic and periodic manual antifoam agent additions (struktol 1647). During cultivation $pO_2$ saturation was maintained above 1% by manually adjusting agitation, aeration and pressure. Agitation rates were between 200-460 rpm, aeration 70-80 l/min and overpressure 0-250 mbar. Cultivation active volume was 52 kg.

Cultivation parameters for oil production during continuous operation were: dilution rate 0.04 $h^{-1}$ (only including feed from biomass production step, not including glucose addition, 100 ml overflow of biomass production was fed to oil production bioreactor every 15 min), volume approximately 9 l, temperature 29-30° C., pH was adjusted to 4.0 with 3 M NaOH and foaming was controlled by automatic and periodic manual antifoam agent additions (struktol J647). During cultivation $pO_2$ saturation was maintained at 5-20% by manual adjusting of agitation and aeration. Agitation rates were between 450-590 rpm, aeration 8 l/min. Oil production cultivation was fed with sterile 50% glucose solution to maintain glucose concentration between 5-60 g/l.

Oil productivity was calculated based on the dilution rates.

In biomass production, bioreactor biomass concentration varied between 18-21 g/l during continuous cultivation. In oil production bioreactor, biomass concentration was 48-58 g/l and biomass oil content in varied between 31-40% of CDW. The average overall microbial oil productivity for 145 h period of continuous operation was 0.98 g/(l*h).

Example 5—*Rhodosporidium fluviale*, Lipid Production in Two Step Continuous Cultivation with Interim Concentration Culture media were prepared as batches in medium sterilization tank and transferred to media tanks for storage. Microbial culturing was started with a batch phase in biomass production bioreactor to allow cells to propagate before the start of continuous operation. Similar biomass propagation was not performed in oil production bioreactor.

After suitable propagation time continuous culturing was started. Biomass production bioreactor was continuously fed with media from media storage tanks. Biomass production bioreactor was operated in overflow mode and culture was continuous transferred forward via dip tube.

As the bioreactors used for the demonstration were very different in size, in order to achieve intended dilution rates in oil production bioreactor, only portion of the culture from biomass production was directed to oil production. Rest of the culture from biomass production bioreactor was directed to biomass waste collection tank. During continuous operation oil production bioreactor was also continuously fed with glucose solution. The feeding rate depended on the sugar consumption. Similarly to biomass production, oil production was operated in overflow mode and culture was continuously transferred to collection tank via dip tube.

After starting of the continuous operation, biomass interim concentration was started. Membrane filtration unit was connected to oil production bioreactor. Culture from oil production bioreactor was pumped to membrane filter, the retentate was circulated back to bioreactor and permeate was removed to collection tank while maintaining continuous operation of the bioreactor.

Culture medium for laboratory inoculum production consisted of (per liter of water): 40 g glucose, 5 g yeast extract, 2.5 g $(NH_4)_2SO_4$, 0.83 g $MgCl_2 \times 6H_2O$, 0.53 g $K_2HPO_4$, 1 g $KH_2PO_4$ and 0.2 g $CaCl_2 \times 2H_2O$. Media components were dissolved in tap water. Medium divided in 50 ml batches was sterilized by autoclaving at 121° C. for 20 min. Preculture media were inoculated with 1% inoculum of *Rhodosporidium fluviale* CBS 9465 yeast and incubated at 29° C. temperature for 26 hours in orbital shaker using 250 rpm agitation rate.

Culture media for cell propagation cultivation and continuous culturing for product formation start up composed of (per liter of water): 60 g glucose, 5 g yeast extract, 4.6 g $KH_2PO_4$, 0.03 $MnSO_4 \times H_2O$, 0.08 $CaCl_2 \times 2H_2O$, 0.0008 $ZnSO_4 \times 7H_2O$, 0.00025 $CuCl \times 2H_2O$, 0.0002 g $Na_2MoO_4 \times 2H_2O$, 0.0024 g $FeSO_4 \times 7H_2O$, 0.19 Struktol, 0.5 g $(NH_4)_2SO_4$, 0.5 g $MgSO_4 \times 7H_2O$, 0.8 g $MgCl_2 \times 6H_2O$, 0.1 g chloramphenicol, 0.0000125 g biotin, 0.00125 thiamin HCl, 0.00025 g vitamin B12, 0.00125 g pantothenic acid. With the exception of ammonium and magnesium salts, all minerals, glucose, yeast extract and struktol were dissolved in tap water and the medium base was in situ sterilized at 121° C. for 30 min forming the medium base. Separate stock solutions were prepared of ammonium and magnesium salts. Solutions were sterilized by autoclaving at 121° C. for 20 min and added aseptically to the sterilized medium base. Vitamins were dissolved in MQ water, sterile filtered and added aseptically to the sterilized medium base. Chloramphenicol was dissolved in ethanol and added aseptically to the sterilized medium base. Oil production bioreactor was filled with water and sterilized.

Biomass propagation medium was inoculated with 1.4% preculture. Working volume of the cultivation was 70 l. Cultivation parameters for biomass propagation culturing were: temperature 29° C., pH was maintained at 5.5 by adjusting with 3 M $NH_4OH$, aeration rate was 1 vvm and agitation rate was 250 rpm.

After 21 h cell propagation in biomass production bioreactor, continuous two step fermentation was initiated by starting the medium feed from medium storage tanks to biomass production bioreactor, culture transfers from biomass production to oil production bioreactor and to collection tank, biomass transfer from oil production bioreactor to collection tank and glucose feed to oil production bioreactor.

After start-up of continuous cultivation culture media composed of (per liter of water): 70 g glucose, 8 g yeast extract, 7 g $KH_2PO_4$, 0.03 $MnSO_4 \times H_2O$, 0.08 $CaCl_2 \times 2H_2O$, 0.0008 $ZnSO_4 \times 7H_2O$, 0.00025 $CuCl \times 2H_2O$, 0.0002 g $Na_2MoO_4 \times 2H_2O$, 0.0024 g $FeSO_4 \times 7H_2O$, 0.19-0.38 Struktol, 0.5 g $(NH_4)_2SO_4$, 0.06-1.47 g $MgSO_4 \times 7H_2O$, 0-1.16 g $MgCl_2 \times 6H_2O$, 0.1 g chloramphenicol, 0.0000125 g biotin, 0.00125 thiamin HCl, 0.00025 g vitamin B12, 0.00125 g pantothenic acid. Medium preparation was similar to preparation of preculture medium.

Cultivation parameters for biomass production during continuous operation were following. During continuous operation flow rate to biomass production bioreactor was 14.3 l/h. Temperature was 29° C., pH was adjusted to 5.0 with 3 M $NH_4OH$ and foaming was controlled by automatic and periodic manual antifoam agent additions (struktol 1647). During cultivation $pO_2$ saturation was maintained above 20% by manually adjusting agitation, aeration and pressure. Agitation rates were between 200-400 rpm, aeration 65-70 l/min and overpressure 22-178 mbar. Cultivation active volume varied between 34-66 kg.

Cultivation parameters for oil production during continuous operation were: dilution rate 0-0.13 $h^{-1}$, active culturing volume was approximately 7.6 l, temperature 29° C. and foaming was controlled by automatic and periodic manual antifoam agent additions (struktol J647). During cultivation $pO_2$ saturation was maintained at 5-30% by manual adjusting of agitation and aeration. Agitation rates were between 150-830 rpm, aeration 6-8 l/min. Oil production cultivation was continuously fed with sterile 40% glucose solution to maintain glucose concentration between 10-60 g/l.

Concentration step in oil production bioreactor was initiated after 165 h cultivation. Membrane filtration unit (Pellicon 2 Mini with three Millipore Durapore 0.45 μm cassettes) was connected to oil production bioreactor. Culture from oil production bioreactor was pumped to membrane filter, the retentate was circulated back to bioreactor and permeate was removed to collection tank while maintaining continuous operation of the bioreactor. Feed flow rate was adjusted based on concentration performance. Dilution rate varied between 0-0.13 $h^{-1}$. Periodically the filtration unit was disconnected from the bioreactor system for cleaning and maintenance.

Oil productivity was calculated based on dilution rates.

In biomass production bioreactor biomass concentration varied between 19-36 g/l during continuous cultivation. Similarly in oil production bioreactor biomass concentration varied between 42-85 g/l and biomass oil content varied between 32-45% of CDW. As the filtration system was periodically separated from the system for maintenance, genuine steady state operation was not achieved. However, on average, when the system was operated with interim concentration, for 316 h period, the lipid productivity was 1.15 g/(l*h). The average time included the downtime e.g. caused by filter unit maintenance. If the downtime is disregarded, the average overall lipid productivity was 1.22 g/(l*h). This was 20% increase to productivity compared to two step continuous culturing without interim concentration.

The invention claimed is:

1. A method for producing a biosynthetic product in a cascade of bio-reactors, the cascade having a bioreactor system for biomass production with at least one biomass production reactor, and a bioreactor system for product formation having at least one product formation reactor in flow connection with a concentration device, which method comprises:
   a) culturing a microorganism in a biomass production reactor by feeding the reactor with nutrient rich culture medium allowing efficient growth of biomass;
   b) taking at least part of a microorganism culture from the bio-mass production reactor of step a) and feeding it to a product formation reactor containing nutrient depleted medium enhanced for formation of the biosynthetic product; and
   c) producing the biosynthetic product in a presence of the nutrient depleted medium in the product formation reactor,
   the method further comprising:
   increasing a cell mass concentration of the microorganism culture of the product formation reactor by using a concentration device in flow connection with the product formation reactor;
   obtaining a microorganism rich fraction by a method selected from the group consisting of centrifugation, filtration, settling, flocculation, flotation, and decanting, at a temperature between 3 to 30° C. lower than a temperature of the reactor from which the microorganism culture was taken and/or lowering a temperature of the microorganism culture to be fed into the concentration device by 3 to 30° C.; and
   regulating a speed by which said at least part of the microorganism culture is taken from the biomass production reactor so as to keep a cell density and nutrient content at a level which keeps cells growing exponentially,
wherein the microorganism is a fungus, yeast, algae, bacterium, archaebacterium, and/or a microorganism capable of producing the biosynthetic product;
wherein the product formation reactor of step b) is a first product formation reactor downstream of the bio-mass production reactor of step a).

2. The method according to claim 1, wherein the concentration device is arranged between the biomass production reactor and the product formation reactor.

3. The method according to claim 2, wherein at least part of the microorganism culture taken from the biomass production reactor is fed into the concentration device arranged between the biomass production reactor and the product formation reactor to obtain a microorganism rich fraction, which is fed into the product formation reactor.

4. The method according to claim 3, comprising:
taking at least part of the microorganism culture from the product formation reactor and feeding it into the concentration device arranged between the biomass production reactor and the product formation reactor or down-stream of the product formation reactor to obtain the microorganism rich fraction, which is fed into the same or subsequent product formation reactor downstream in the cascade.

5. The method according to claim 3, wherein the biomass production reactor is a last biomass production reactor of the cascade and the product formation reactor is a first product formation reactor of the cascade.

6. The method according to claim 5, wherein the bioreactor system for biomass production comprises:
at least 2, 3, 4, 5, 6, 7, or 8 bioreactors.

7. The method according to claim 6, wherein the bioreactor system for product formation comprises:
at least 2, 3, 4, 5, 6, 7, or 8 bioreactors.

8. The method according to claim 1, wherein the concentration device is arranged downstream of the product formation reactor.

9. The method according to claim 8, comprising:
taking at least part of the microorganism culture from the product formation reactor and feeding it into the concentration device arranged between the biomass production reactor and the product formation reactor or down-stream of the product formation reactor to obtain the microorganism rich fraction, which is fed into the same or subsequent product formation reactor downstream in the cascade.

10. The method according to claim 1, wherein the biomass production reactor is a last biomass production reactor of the cascade and the product formation reactor is a first product formation reactor of the cascade.

11. The method according to claim 1, wherein a bioreactor system for biomass production comprises:
at least 2, 3, 4, 5, 6, 7, or 8 bioreactors.

12. The method according to claim 1, wherein a bioreactor system for product formation comprises:
at least 2, 3, 4, 5, 6, 7, or 8 bioreactors.

13. The method according to claim 1, wherein a bioreactor system or the cascade of serially connected bioreactors is operated in a continuous manner.

14. The method according to claim 1, comprising:
enhancing one or more biomass production bioreactors of the cascade for microorganism growth at late stage exponential phase; and/or
enhancing the product formation reactor subsequent to the biomass production bioreactor for biosynthetic product formation at a stationary growth phase, and/or under nutrient starvation conditions; and/or
enhancing any additional product formation reactor for biosynthetic product formation with minimal carbon source addition.

15. The method according to claim 1, wherein the biosynthetic product is one or more of the following:
i) biomass from the cultured microorganism;
ii) a primary metabolite;
iii) a secondary metabolite;
iv) an intracellular product; and/or
v) an extracellular product.

16. The method according to claim 1, wherein the biosynthetic product is an intracellular product.

17. The method according to claim 1, wherein the biosynthetic product is one or more lipids selected from the group consisting of long chain diacids, hydroxyl fatty acids, long chain diols, lipids, fats, oils, waxes, farnesene type products, wax esters, sterols, terpenoids, isoprenoids, carotenoids, polyhydroxyalkanoates, nucleic acids, fatty acids, fatty acid derivates, fatty alcohols, fatty aldehydes, fatty acid esters, fatty amines, medium and long chain dicarboxylic acids, epoxy fatty acids, long chain diols and polyols, phospholipids, glycolipids, sphingolipids and acylglycerols.

18. The method according to claim 1, wherein the method is free of feeding the at least part of the microorganism culture from the bio-mass production reactor of step a) to a product formation reactor containing nutrient rich medium.

19. The method according to claim 1, wherein the microorganism rich fraction is obtained at a temperature between 3 to 25° C. lower than the temperature of the reactor from which the microorganism culture was taken and/or wherein the temperature of the microorganism culture to be fed into the concentration device is lowered by 3 to 25° C.

20. The method according to claim 1, wherein the microorganism rich fraction is obtained at a temperature between 3 to 15° C. lower than the temperature of the reactor from which the microorganism culture was taken and/or wherein the temperature of the microorganism culture to be fed into the concentration device is lowered by 3 to 15° C.

* * * * *